(12) United States Patent
Carbonell

(10) Patent No.: US 8,101,425 B1
(45) Date of Patent: Jan. 24, 2012

(54) PARTICLES EMBEDDED IN A POROUS SUBSTRATE FOR REMOVING TARGET ANALYTE FROM A SAMPLE

(75) Inventor: Ruben G. Carbonell, Raleigh, NC (US)

(73) Assignee: Pathogen Removal and Diagnostic Technologies Inc., Wilmington, DE (US)

( * ) Notice: Subject to any disclaimer, the term of this patent is extended or adjusted under 35 U.S.C. 154(b) by 84 days.

(21) Appl. No.: 11/570,210

(22) PCT Filed: Jun. 9, 2005

(86) PCT No.: PCT/US2005/020036
§ 371 (c)(1),
(2), (4) Date: Apr. 24, 2007

(87) PCT Pub. No.: WO2005/123952
PCT Pub. Date: Dec. 29, 2005

Related U.S. Application Data

(60) Provisional application No. 60/578,061, filed on Jun. 9, 2004, provisional application No. 60/616,118, filed on Oct. 6, 2004, provisional application No. 60/617,669, filed on Oct. 13, 2004.

(51) Int. Cl.
*G01N 21/77* (2006.01)
(52) U.S. Cl. ........ 436/170; 436/518; 436/528; 436/531; 436/532; 436/169; 422/420; 422/421; 422/425; 422/426
(58) Field of Classification Search .......... 436/518, 436/528, 531, 532, 535, 169, 170; 435/7.1, 435/283.1, 287.2; 422/420, 421, 425, 426
See application file for complete search history.

(56) References Cited

U.S. PATENT DOCUMENTS

| | | | |
|---|---|---|---|
| 3,993,451 A * | 11/1976 | Verbeck | 422/428 |
| 4,011,067 A | 3/1977 | Carey, Jr. | |
| 4,342,811 A | 8/1982 | Lopatin et al. | |
| 4,433,024 A | 2/1984 | Eian | |
| 4,550,123 A | 10/1985 | Lopatin et al. | |
| 4,604,203 A | 8/1986 | Kyle | |
| 4,797,318 A | 1/1989 | Brooker et al. | |
| 4,895,806 A | 1/1990 | Le et al. | |
| 4,957,943 A | 9/1990 | McAllister et al. | |
| 4,959,305 A | 9/1990 | Woodrum | |
| 4,959,307 A * | 9/1990 | Olson | 435/7.91 |
| 5,141,850 A | 8/1992 | Cole et al. | |
| 5,328,758 A | 7/1994 | Markell et al. | |
| 5,827,477 A * | 10/1998 | Macho et al. | 252/408.1 |
| 5,938,650 A * | 8/1999 | Baer et al. | 604/368 |
| 5,985,675 A | 11/1999 | Charm et al. | |
| 6,200,474 B1 | 3/2001 | Kopaciewicz et al. | |
| 6,218,134 B1 | 4/2001 | Yamauchi et al. | |
| 6,379,622 B1 | 4/2002 | Polak et al. | |
| 6,451,260 B1 | 9/2002 | Dusterhoft et al. | |

(Continued)

FOREIGN PATENT DOCUMENTS

RU 2130969 5/1999

(Continued)

*Primary Examiner* — Melanie J Yu
(74) *Attorney, Agent, or Firm* — LeClairRyan, a Professional Corporation

(57) ABSTRACT

The invention provides devices, test kits and methods for removing target agents from a sample. The device contains one or more porous matrices having pore sizes larger than 10 μm, and a plurality of particles impregnated therein. The target agents attach the device and are removed from the sample.

18 Claims, 9 Drawing Sheets

U.S. PATENT DOCUMENTS

| | | |
|---|---|---|
| 6,544,732 B1 | 4/2003 | Chee et al. |
| 6,555,061 B1 * | 4/2003 | Leong et al. ............... 422/412 |
| 6,884,494 B1 * | 4/2005 | Curro et al. ............... 428/196 |
| 7,767,878 B2 * | 8/2010 | Suzuki ............... 604/372 |
| 2001/0008774 A1 | 7/2001 | May et al. |
| 2003/0044799 A1 | 3/2003 | Matson |
| 2003/0073121 A1 | 4/2003 | Mendel-Hartwig et al. |
| 2003/0148544 A1 | 8/2003 | Nie et al. |
| 2003/0211471 A1 | 11/2003 | Hammond et al. |
| 2003/0228430 A1 * | 12/2003 | Tanaka et al. ............. 428/32.39 |
| 2005/0032244 A1 | 2/2005 | Nie et al. |
| 2005/0090021 A1 | 4/2005 | Walt et al. |
| 2006/0160064 A1 | 7/2006 | Carbonell |

FOREIGN PATENT DOCUMENTS

| | | |
|---|---|---|
| WO | 91/15771 | 5/1991 |
| WO | 9301880 A1 | 4/1993 |
| WO | 9306924 A1 | 4/1993 |
| WO | 03003015 A2 | 1/2003 |

* cited by examiner

PARTICLES EMBEDDED IN A POROUS SUBSTRATE FOR REMOVING TARGET ANALYTE FROM A SAMPLE

CROSS REFERENCE TO RELATED APPLICATIONS

This application is a national stage application under 35 U.S.C. §371 from PCT Application No. PCT/US2005/020036, filed Jun. 9, 2005, which claims benefit under 35 U.S.C. §119(e) based on U.S. Provisional Application No. 60/617,669, filed Oct. 13, 2004, U.S. Provisional Application No. 60/616,118, filed Oct. 6, 2004, and U.S. Provisional Application No. 60/578,061, filed Jun. 9, 2004, the entire contents of which are incorporated herein by reference.

I. FIELD OF THE INVENTION

This invention relates to devices and methods for removal of target agents from a sample. In particular, the invention relates to removal of pathogens from biological samples.

II. BACKGROUND OF THE INVENTION

The process of adsorption of biological species to solid supports finds a number of practical applications in purification, detection and removal of target molecules from multi-component streams. For example, ion exchange, hydrophobic and affinity ligands are able to adsorb many agents preferentially to chromatographic supports to affect their separation from aqueous solutions. Once adsorbed, the biological agent can either be eluted as a product, or detected by ELISA and other analytical approaches.

In some instances, the solution containing the target biological agent also contains large entities such as red blood cells, viruses, bacteria, liposomes, leukocytes, and aggregates of various sizes. In many of these instances, it is desirable to allow the large aggregates to flow through the solid matrix or support without interfering with the ability of the target biological agents to bind to the support. This requires pore spaces in the solid matrix that are large enough to accommodate the flow of the large entities. Unfortunately, large pore spaces can have a low surface area that limits the capacity of the solid matrix to bind to the target agents.

In other cases, it is desirable to actually filter the large particles to facilitate adsorptive separation of the smaller target agents. One example is the removal of cells from a culture medium to recover an extracellular product.

In addition, there are many instances where it is desirable to bind, rather than filter, the biological entities that are very large. For example, it is of importance to adsorb specifically many pathogens, including infectious prions, viruses, bacteria, and toxins from mixtures of biological agents. These entities often have difficulty accessing the small pores that are required for binding in the currently available sample purification and separation devices.

Nonwoven fibers or webs, also referred to as melt blown polymer fibers or spunbonded webs, are well known and are used for filtration and separation of fine particles from air and aqueous solutions. (see, for example, U.S. Pat. Nos. 4,011,067 and 4,604,203, each of which is incorporated herein by reference in its entirety). Loading of sorptive particulates in nonwoven webs is also well known in the art (see, for example, U.S. Pat. Nos. 4,433,024; 4,797,318; and 4,957,943, each of which is incorporated herein by reference in its entirety). Applications include face respirators for removing particulates and gaseous contaminants, protective garments, fluid retaining articles, and wipers for oil.

More recently, methods for the fabrication of particle impregnated nonwoven fabrics for separation and purification have been reported. See, for example, U.S. Pat. No. 5,328,758, incorporated herein by reference in its entirety. The patent teaches functionalized particles for the attachment of affinity ligands. It is disclosed that the particles are blown into the polymer fibers during the melt blowing stage. The nonwoven fabric comprises pores having pore sizes in the range of 0.24 to 10 µm, preferably 0.5 to 5 µm. It is also specified that the impregnated fabric material must have a Gurley Time of at least 2 seconds.

WO93/01880 discloses a leukocyte-removing nonwoven fabric filter material produced by dispersing in a medium a mass of a great number of small fiber pieces having a fiber diameter of not more than 0.01 µm and a length of about 1 to 50 µm, together with spinable and weavable short fibers having an average length of 3 to 15 mm. U.S. Pat. Nos. 4,550,123 and 4,342,811, each of which is incorporated herein by reference in its entirety, describes microporous polymeric fibers and films which contain particles capable of sorbing vapors, liquids, and solutes. Typical sorbent particles include active carbon, silica gel, and molecular filter type materials.

The invention as disclosed herein provides devices and methods for sample purification, and detection and removal of target agents from a sample with increased efficiency and specificity and substantial savings in time and cost over the devices of the prior art.

III. SUMMARY OF THE INVENTION

The invention, as disclosed and described herein, provides methods, devices and kits for removing target agents from a sample.

In one aspect, the invention provides a device for separating at least one target agent from a sample. The device contains one or more porous matrices having pore sizes larger than 10 µm, and a plurality of particles impregnated therein, wherein the at least one target agent attaches to the one or more porous matrices, particles, or both and is removed from the sample. In one embodiment, the porous matrix, the particles or both have uniform or variable pore sizes. In another embodiment, the particles have a pore size of about 0.001 µm to about 0.1 µm. In yet another embodiment, the particles comprise a porous resin having interconnected pores with surface areas in the range of about 1-2 $m^2/g$ of dried resin to about 300 $m^2/g$ of dried resin.

In yet another embodiment, the porous matrix comprises natural fibers, synthetic fibers or both. In a preferred embodiment, the porous matrix comprises at least one nonwoven fabric. In another embodiment, the porous matrix is a blend of two or more of the same or different types of woven and/or nonwoven fabrics.

In yet another embodiment, the device of claim 1, wherein the particles comprise a polymethacrylate, a methacrylate resin, a modified resin, or a combination thereof.

In one embodiment, the device contains a modified resin and one or more porous matrices comprise plasma treated polypropylene that is functionalized with a reactive group comprising a ligand having a primary amine and a hydrophilic spacer containing polyethylene glycol units.

In another embodiment, the particles are sandwiched between the one or more porous matrices.

In one embodiment, the particles, the porous matrix or both are functionalized with one or more reactive groups. The target agents are attached to the particles, porous matrix or both via absorption, adsorption, ion exchange, covalent bonds, hydrophobic, dipole, quadrupole, hydrogen bonding, specific interactions, formation of charged species, via affinity interaction to specific ligands, or a combination thereof. In yet another embodiment, the particles are polymethacrylate or a methacrylate resins including, by way of example and not limitation, a FRACTOGEL™ EMD, a TOYOPEARL™, or a TSK-GEL™ polymer matrix. In yet another embodiment, the resin is TOYOPEARL™ Amino 650 including, for example, Amino 650 U, Amino 650 M, or a partial acetylated form of the Amino 650M or Amino 650 U. Partial acetylated resin includes from about 5% to about 95% or more acetylated resins. In one embodiment, partial acetylated resin includes from about 10% to about 85% acetylated resin. In another embodiment, partial acetylated resin includes from about 20% to about 75% acetylated resin. In yet another embodiment, partial acetylated resin includes from about 30% to about 60% acetylated resin. In another embodiment, partial acetylated resin includes from about 40% to about 60% acetylated resin. It is intended herein that by recitation of such specified ranges, the ranges recited also include all those specific integer amounts between the recited ranges. For example, in the range about 40 and 60%, it is intended to also encompass 45%, 50%, 55%, 57%, etc, without actually reciting each specific range therewith. In another embodiment, the resin includes wet resins e., fully pre-hydrated), dry resins (i.e., not pre-hydrated before contact with the sample, and/or previously dry but hydrated before contact with the sample). The use of a partial acetylated dry and/or wet resin is also encompassed within the scope of the invention.

In another aspect, the device contains a functionalized porous nonwoven or woven matrix that has the ability to adsorb the target agents. In one embodiment, the device contains a nonporous matrix as well as porous matrix, one or both of which matrices may be functionalized. In another embodiment, the porous matrix contains uniform or variable pore sizes larger than 10 µm.

In yet another aspect, the invention provides methods of separating at least one target agent from a sample comprising; (a) providing a sample potentially containing one or more target agents; (b) providing a device comprising (i) one or more porous matrices having pore sizes larger than 10 µm, and (ii) a plurality of particles impregnated in the porous matrix, wherein the particles have the capacity of attaching at least one target agent; (c) subjecting the sample to the device; (d) attaching at least one target agent to the particles, to the one or more porous matrices or both; and (e) separating at least one target agent from the sample.

In another aspect, the invention provides test kits for target separation, detection and sample purification comprising one or more of the following (i) a device containing a porous matrix having pore sizes larger than 10 µm, and a plurality of particles impregnated therein, (ii) a container containing one or more of buffers, reagents, chemical agents, functionalization reagents, enzymes, detection agents, control materials, (iii) instructions for use of the test kit, and (iv) packaging materials.

Other preferred embodiments of the invention will be apparent to one of ordinary skill in the art in light of what is known in the art, in light of the following drawings and description of the invention, and in light of the claims.

IV. BRIEF DESCRIPTION OF THE DRAWINGS

FIG. 1 Depicts a schematic representation for resin impregnated nonwoven fabrics (RINs). The nonwoven fabrics have a pore size of about 12 µm and are impregnated with a porous resin support. The mean pore size is sufficiently large to allow red blood cells to flow freely through the device without exhibiting any signs of damage. Particles (10), fibers (20), impregnated particles (11), and nonwoven fabric (21) are shown therein.

FIG. 2 Depicts a schematic representation of a device composed of square sheets of a nonwoven or woven fabric. A staggered array of sheets of nonwoven or woven fabric is coated with affinity ligands on both sides. The sample flows in the tortuous path between the sheets. The pore size of the sheets is adjusted according to the desired application.

FIG. 3 Depicts a scanning electron micrograph of sample 13 inner/inner layer calendered at 150 F, and 100 pounds per linear inch (PLI) with resin. The micrograph shows pocket areas of sample 13 at 50× magnification.

FIG. 4 Depicts a scanning electron micrograph of sample 11 inner/outer layer calendered at 180 F, and 400 PLI, with resin. The micrograph shows pocket areas of sample 11 at 50× magnification.

V. DETAILED DESCRIPTION OF THE INVENTION

Figure 1:
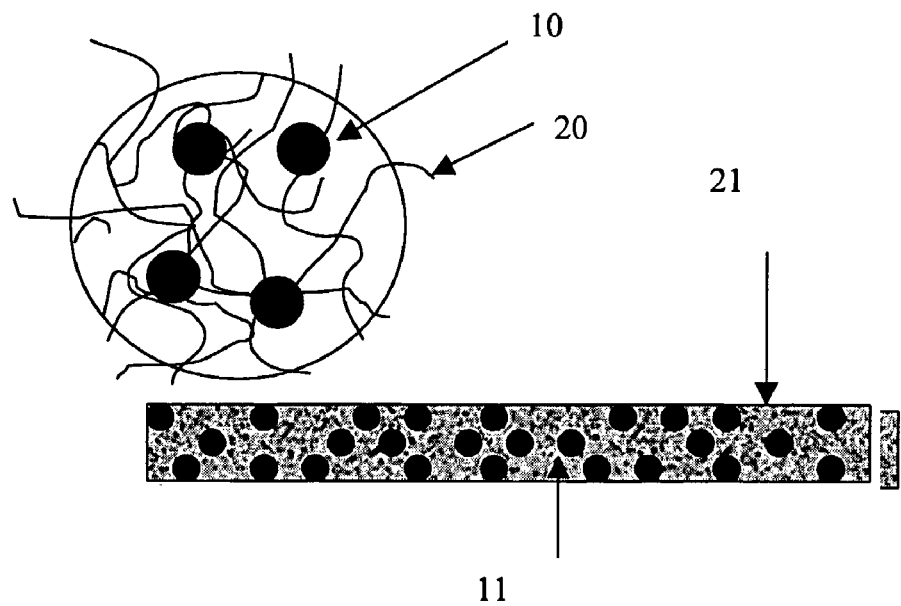

Methods, devices and kits for efficient separation of target molecules from a sample are described herein. The methods, kits and devices of the invention are useful in a variety of applications including purification, separation, and processing of expressed gene products from cells, production and delivery of biopharmaceuticals, and prognostic, diagnostic, and/or detection applications, among others. The invention described herein defines novel devices that separate different components of a sample and allow the flow of larger species through the device while providing large surface areas to bind the target agents.

Particular applications of this invention involve the removal of pathogens such as prions, viruses, fungus, bacteria and toxins from a biological samples such as, for example, a blood sample including whole blood, red blood cell containing compositions, red blood cell concentrates, platelets concentrates, plasma, plasma derivatives, leukocytes, leukodepleted blood, mammalian cell culture, fermentation broths and other media used for the manufacture and delivery of biopharmaceuticals and the preparation of therapeutics.

1. Definitions

The definitions used in this application are for illustrative purposes and do not limit the scope of the invention.

As used herein, "modified resins" are defined broadly within the scope of the invention and include analogues, variants and functional derivatives of a resin with or without a functional group. The modification includes for example, substitution, deletion, or addition of chemical entities (e.g., amino acids) to a particular resin, or its functional group, or both. For example, amino substitution, acetylation, and/or partial acetylation of resins are included in the definition of modified resins.

As used herein, "target agents" are defined broadly within the scope of the invention and include chemical, biological, or physical agents that are captured by the device of the invention. Target agents include molecules, compounds, cell constituents, organelles, aggregates, toxin, prions, and microorganisms such as pathogens including, virus, bacteria, fungi, and protozoa, among others. Target molecules also include polymeric molecules such as polynucleotide molecules, for example, DNA, RNA, DNA-RNA hybrid, antisense RNA, cDNA, genomic DNA, mRNA, ribozyme, natural, synthetic, or recombinant nucleic acid molecules, oligopeptides, oligonucleotides, peptides, peptide-nucleic acid hybrids, antigen, antibody, antibody fragments, large proteins and aggregates such as vWF:FVIII, and HDL among others.

As used herein, the term "pathogen" is intended to mean any replicable agent that can be found in or infect a biological sample such as a blood sample. Such pathogens include the various viruses, bacteria, protozoa, and parasites known to those of skill in the art to generally be found in or infect whole blood or blood components and other pathogenic contaminants not yet known. Illustrative examples of such pathogens include, but are not limited to, bacteria, such as *Streptococcus* species, *Escherichia* species and *Bacillus* species; viruses, such as human immunodeficiency viruses and other retroviruses, herpes viruses, paramyxoviruses, cytomegaloviruses, hepatitis viruses (including hepatitis A, hepatitis B, and hepatitis C viruses), pox viruses and toga viruses; and parasites, such as malarial parasites, including plasmodium species, and trypanosomal parasites.

As used herein, "sample" includes any sample containing a target agent that can be captured by the device and method of the invention. Samples may be obtained from any source that potentially contains a target agent. Such sources include animals, plants, soil, air, water, fungi, bacteria, and viruses, among others. Animal samples are obtained, for example from tissue biopsy, blood, hair, buccal scrapes, plasma, serum, skin, ascites, plural effusion, thoracentesis fluid, spinal fluid, lymph fluid, bone marrow, respiratory fluid, intestinal fluid, genital fluid, stool, urine, sputum, tears, saliva, tumors, organs, tissues, samples of in vitro cell culture constituents, fetal cells, placenta cells or amniotic cells and/or fluid, among others.

As used herein, "cell culture media" includes any prokaryotic or eukaryotic culture media such as, for example, bacterial, yeast and other microbiological cell culture media, mammalian cell culture media, plant cell culture, and insect culture, fermentation broths and other media used for the production and delivery of biopharmaceuticals and the preparation of therapeutics.

As used herein, "blood sample" includes, for example and not by way of limitation, whole blood, red blood cell-containing compositions (e.g., red blood cell concentrates and platelets concentrates), leukocytes, and leukodepleted blood, blood proteins, such as blood clotting factors, enzymes, albumin, plasminogen, and immunoglobulins; and liquid blood components, such as plasma, plasma derivatives, and plasma-containing compositions among other blood samples.

As used herein, the term "red blood cell-containing composition" means whole blood, red blood cell concentrates and any other composition that contains red blood cells. Other than red blood cells, the composition can also contain a biologically compatible solution, such as ARC-8, Nutricell (AS-3), ADSOL (AS-1), Optisol (AS-5) or RAS-2 (Erythrosol), and one or more cellular blood components, one or more blood proteins, or a mixture of one or more cellular blood components and/or one or more blood proteins. Such compositions may also contain a liquid blood component, such as plasma.

As used herein, "particle" means organic or inorganic porous or nonporous forms having a diameter of about 1 to about 200 µm or more, these include, for example and not by way of limitation, fibers with a length to diameter ratio of about 1 µm to about 20 µm or more, in addition to sorptive particles such as granules, beads, resins, or powders, among others.

As used herein, "sorbent" "sorptive" or "sorption" means capable of taking up and holding by either absorption or adsorption.

As used herein, "attachment" is broadly defined within the scope of the invention and includes any type of physical, chemical, or biological bonding processes between two entities and includes, for example and not by way of limitation, absorption, adsorption, covalent bonding, ion exchange, hydrophobic, hydrogen bonding, dipole, quadrupole or affinity interaction, formation of charged species, the attachment of affinity ligands (e.g., including peptides, oligonucleotides, proteins, spacer arms, hydrophobic moieties, fluorinated materials), among others.

As used herein, "spiked solution" refers to a solution that has received a certain amount of the target protein, toxin, virus, bacteria, or other organism, in its pure, partially purified, or crude form.

2. Porous Matrix

The devices of the present invention comprise a porous matrix having particles impregnated therein. Selection of a porous matrix can vary widely within the scope of the invention. Useful matrices include woven and nonwoven fabrics (such as fibrous webs), microporous fibers, and microporous membranes. These fibers can be made out of any materials and any methods known to the art, including meltblowing, spinbonding, and electro spinning.

Fibrous webs are particularly desired because such webs provide large surface areas, with nonwoven fibrous webs being preferred due to ease of manufacture, low material cost, and allowance for variation in fiber texture and fiber density. A wide variety of fiber diameters, e.g., 0.05 to 50 µm, is used in the preparation of the device of the present invention. The matrix thickness is varied to fit the desired utility of the device, e.g., about 0.1 µm to about 100 cm thick or more. The matrix can be used in the form of a single sheet or stacked as desired to achieve the desired capacity for adsorption. In one embodiment, calendering or pressurizing of the porous matrix is required in order to achieve the desired thickness and pore size. The porous matrix of the devices of the invention is made from a wide variety of natural and synthetic fibers, according to the precise physical and chemical properties of the porous matrix intended for the end application. The porous matrix of the invention is selected from natural or synthetic sources including, for example, polyester, polypropylene, rayon, aramid, and/or cotton, among others.

Also encompassed within the scope of the present invention is the use of two or more different matrices with different chemical or physical characteristics. In one embodiment of the present invention, the porous matrix is a blend of two or more of the same or different types of woven and/or nonwoven fabrics. In another embodiment, a hybrid of two or more porous matrices with different pore sizes is used, one matrix having smaller pore sizes acts to capture the smaller materials whereas the other matrix having larger pore sizes acts as a filter for larger materials (leukocytes for example). In another embodiment, a functionalized porous matrix for affinity separations having a predetermined pore size is placed within another membrane as a support.

2.1. Nonwoven Fabrics

Nonwoven fabrics are random fibrous webs, formed by mechanical, wet or air laid means and having interconnecting open areas through the cross section. Nonwoven fabrics are usually flat, porous sheets that are made directly from separate fibers or from molten plastic or plastic film. These fabrics are broadly defined as sheet or web structures bonded together by, for example, entangling fiber or filaments or perforating films mechanically, thermally or chemically using various techniques including adhesive bonding, mechanical interlocking by needling or fluid jet, entanglement, thermal bonding, and stitch.

Typically, nonwoven fabrics have mean pore flow (MPF) diameters ranging from about 1 to about 500 μm. In one embodiment, the porous matrix has a pore size of at least 10 μm. In a preferred embodiment, the porous matrix has a pore size of more than 10 μm. In yet another embodiment, the porous matrix has a pore size of more than 15 μm. It is intended herein that by recitation of such specific numerical values, the values recited also include all those specific integer amounts between the recited values. For example, more than 10 μm is intended to also encompass 12, 20, 30, 45, 70, 100, 200, 300, 400 and 500 μm, etc., without actually reciting each specific range therein.

The mean pore diameter of the fabric can be chosen to correspond to the desired pore diameter for flow of the large aggregates in the biological mixture. For example, in the case of red blood cells, pore flow diameter would be on the order of about 12 μm. In this case, any porous or non-porous particle with diameters much beyond 12 μm would be trapped in the spaces between the fibers and particles would still be available for adsorption of the target species. As a result, significantly smaller diameter particles can be used for adsorption while allowing flow of the larger species through the pore spaces.

Nonwoven fabrics are made of fibers that, depending on the fabrication method, have diameters in the range of, for example, from about 0.01 to about 10 μm. The fibers consist of a wide variety of materials including natural fibers and synthetic fibers. Natural fibers include, for example, cellulose, cotton, and wool, among others. Synthetic fibers include common polymers such as polypropylene and polyester (PET, polyethylene terephthalate). Suitable polymers include polyalkylenes such as polyethylene and polypropylene, polyvinyl chloride, polyamides such as the various nylons, polystyrenes, polyarylsulfones, polyvinyl alcohol, polybutylene, ethyl vinyl acetate, polyacrylates such as polymethyl methacrylate, polycarbonate, cellulosics such as cellulose acetate butyrate, polyesters such as poly (ethylene terephthalate), polyimides, and polyurethanes such as polyether polyurethanes, and combinations thereof.

Nonwoven fabrics can also be prepared from combinations of co-extruded polymers such as polyester and polyalkylenes. Copolymers of the monomers of the polymers described above are also included within the scope of the present invention. Additionally, nonwoven fabrics are combined webs which are an intimate blend of fine fibers and crimped staple fibers. In one embodiment, the nonwoven fabric of the device of the invention also includes a permeable support fabric laminated to one or both sides of the fabric, as described in U.S. Pat. No. 4,433,024 (incorporated herein by reference in its entirety), or additionally contains reinforcing fibers.

Nonwoven fabrics are made by different means, including meltblowing and spinbinding. There are several mechanical approaches to bonding nonwoven fabrics together, for example, membranes are welded together using an ultrasound cutter/sealer or by the use of a press to apply heat and pressure simultaneously. Dry-laid nonwovens contain layers of fibers, each layer containing randomly positioned or parallel fibers. Bonding with an adhesive or heat is necessary for the dry-laid nonwoven fabric. Wet-laid nonwoven fabrics are paper-like nonwovens containing a random array of layered fibers, with the layering resulting from the deposition of fibers from a water slurry. Needlepunched nonwoven fabrics are characterized by the entangled condition of fibers of which they are composed, with the entanglement resulting from the application of heat, moisture and agitation to a fibrous web. Spunlaced nonwoven fabrics have fibers entangled by action of high-velocity water jets (process also called hydroentanglement).

3. Particles

In one aspect, the device of the present invention includes particles as well as the porous matrix. Particles have a capacity to attach the target agents. The particles are porous, non porous or both. In one embodiment, the porous particles are sorbent particles capable of adsorption or absorption of the target agent. The particles are made of one material or a combination of two or more materials, which materials are non-swellable or swellable in organic fluids or aqueous fluids and are substantially insoluble in water or fluids. It has been found advantageous in some instances to employ particles in two or more particle size range falling within the broad range.

Size and shape of the particles can vary widely within the scope of the invention and depend to some extent upon the type of porous matrix support into which such particles are incorporated. For example, particles have a spherical shape, a regular shape, or an irregular shape, or a combination thereof.

Particles used in the device of the invention have an apparent size within the range of about 1-2 μm to about 200-300 μm. In general, differences in useful particle sizes are dictated by the type of the porous matrix in which particles are incorporated, processes and equipment which are utilized to form the porous matrix and the porosity of the matrix so formed. For example, nonwoven fibrous webs and fibrillated polymer matrices can be formulated with the entire size range of particles. Preferably, about 40-200 μm sized particles are used for the nonwovens while 1-100 μm sized particles are preferred for fibrillated polytetrafluoroethylene (PTFE) matrices.

Also included within the scope of the present invention are particles having a wide range of pore sizes. Particles with a relatively large pore size are used for the efficient capture of the larger target molecules, such as proteins, while particles with smaller pore sizes are used for the efficient capture of smaller target molecules. The range of available pore sizes is for example, from about 0.001 μm to about 0.1 μm. In one embodiment, the pore sizes are about 0.1-0.55 μm. In another embodiment, the pore sizes are about 0.6-2 μm. In yet another embodiment, the pore sizes are about 0.25-5 μm or more. It is intended herein that by recitation of such specified ranges, the ranges recited also include all those specific integer amounts between the recited ranges. For example, in the range of about 0.1-0.55 μm, it is intended to also encompass 0.2, 0.3, 0.4, 0.5 μm etc, without actually reciting each specific range therewith.

The particles are made of carbon or an organic compound which can be a polymer or copolymer. For example, particles are made of a copolymer of styrene and divinylbenzene and derivatives thereof, polymethacrylate ester, derivatized azlactone polymer or copolymer, organic coated inorganic oxide particles such as silica, alumina, aluminum oxide, titania, titanium oxide, zirconia, and other ceramic materials, glass, cellulose, agarose, and a wide variety of different polymers, including polystyrene and polymethylmethacrylate, acrylic resins and other types of gels used for electrophoresis, among others.

Other suitable particles for the purposes of this invention include any particle which can be coated with insoluble, swellable, or non-swellable sorbent materials on their external and/or internal surfaces. In one embodiment, the particles swell to a volume of about 2-5 times or more as compared to their original dry weight.

The function of coating is to provide specific functionalities and physical properties, which can be tailored according to the specific separation assay intended. These functions include sorption, ion exchange, chelation, steric exclusion, chiral, affinity, etc. Preferred particle material for such coatings includes inorganic oxide particles, most preferably silica particles. Such particles having coated surfaces are well known in the art, see, for example, Snyder and Kirkland, "Introduction to Modern Liquid Chromatography", 2d Ed., John Wiley & Sons, Inc. (1979) and H. Figge et al., *Journal of Chromatography* 351 (1986) 393-408 and include modified silica particles, silica particles having covalently bonded organic groups including cyano, cyclohexyl, $C_8$ (octyl), and $C_{18}$ (octadecyl) groups. The coatings can be mechanically applied by in situ crosslinking of polymers or can be functional groups covalently bonded to the surface of the particles.

The amount of particles incorporated into the porous matrix can vary widely within the scope of the present invention. Generally, the amount of particles ranges from about 1 to about 99% by volume of the device. Preferably, the amount is greater than 20% by volume, and more preferably greater than 50% by volume. Thus, a device of the present invention can contain up to 95% or more by weight of particles, thereby providing a potentially high capacity for target attachment. The particles of the invention generally withstand a wide range of pH values, for example pH values about 4 or lower to pH values of about 12 or higher.

The particles of the invention are versatile and are used to carry out a variety of chromatographic or non-chromatographic separation assays. Examples of the separation methods contemplated within the scope of the present invention include reverse phase separations, affinity separations, expanded bed separations, ion-exchange chromatography, gel filtration, chromatographic component separation, solid-phase extraction, among other methods of separating, measuring or collecting chemical or biological target agents from other components of a sample. The particles are also used for binding to and thereby separating nucleic acid molecules and/or polypeptide target agents from a sample.

A preferred particle of the device of the invention is a porous resin. Porous resins for adsorption separations are available in a large variety of different materials, including silica, glass, cellulose, agarose, and a wide variety of different polymers, including polystyrene polymethylmethacrylate, polyacrylamide, agarose, hydrogel, acrylic resins and other types of gels used for electrophoresis. Many of the porous adsorption resins such as silica, glass and polymers can be dried and have interconnected pores with surface areas in the range of about 1-2 $m^2/g$ of dried resin to over 300 $m^2/g$ of dried resin. Other types of resins are cross linked gels that cannot be dried without damaging the structure. These types of resins normally do not have a specific surface area since the materials are able to diffuse uniformly through the cross linked matrix.

Also encompassed within the scope of the invention is the use of modified resins including analogues, variants and functional derivatives of a natural or modified resin, or the functional groups thereof. The modification includes for example, substitution, deletion, or addition of chemical entities (e.g., amino acids) to a particular resin, or its functional group, or both. For example, amino substitution, acetylation, and/or partial acetylation of resins are included within the scope of the invention. Any modification to the functional group of a resin is also included within the scope of the modified resins according to the invention.

Other types of natural or modified resins useful within the scope of the invention include, but are not limited to, phenyl sepharose, butyl sepharose, octyl sepharose, polystyrene cross-linked with divinyl benzene, hydrocell C3 polystyrene-divinylbenzene, hydrocell C4 polystyrene-divinylbenzene, hydrocell phenyl polystyrene-divinylbenzene, methyl HIC methacrylate,-Butyl HIC methacrylate, wide-pore-hi-phenyl, fractogel EMD, hydrophobic resin-propyl methacrylate co-polymer fractogel EMD, hydrophobic resin-phenyl methacrylate co-polymer octyl sepharose, phenyl sepharose, Toyopearl HIC, Toyopearl amino-650S, Toyopearl amino-650M, Toyopearl amino-650C, Toyopearl amino-650EC, Toyopearl butyl-650S, Toyopearl butyl-650C, Toyopearl butyl-650M, Toyopearl ether-650S, Toyopearl ether-650C, Toyopearl ether-650M, Toyopearl hexyl-650S, Toyopearl hexyl-650C, Toyopearl hexyl-650M, Toyopearl phenyl-650S, Toyopearl phenyl-650C (PRDT), Toyopearl phenyl-650M, and Toyopearl 659 CU (PRDT) among others. All Toyopearl resins are available commercially from Tosoh Biosep, Montgomeryville, Pa. Sepharose resins are available from GE Healthcare, Piscataway, N.J. Fractogel resins are available from Merck, Darmstadt, Germany. Hydrocell resins are available through BioChrom Labs, Inc., Terre Haute, Ind. The remaining resins are generic names for a variety of base materials for resins that are publicly available.

If porous resins are packed into a column, the hydrodynamic diameter available for flow is determined by the particle diameter and the bed void fraction:

$$D_h = \frac{d_p}{3} \frac{\varepsilon}{1-\varepsilon} \tag{1}$$

wherein $D_h$ is the equivalent hydraulic diameter for flow between particles, dp is the particle diameter, and ε is the void fraction As a result, to allow large species to flow through the column, it is necessary to use large particles that in turn increase the diffusion resistance for adsorption into the resin. For example, to allow red blood cells to flow through the column, around 65 µm diameter particles are necessary to provide 14 µm pore diameter in the interparticle space if the bed porosity is about 0.4.

4. Resin Impregnated Nonwoven Fabrics (RINs)

The incorporation of the particles into the matrix can be accomplished through variety of ways. Since nonwoven fabrics can be made with a controlled mean pore diameter, it is possible to impregnate porous resin particles such as the ones described above, within the fibers making up the nonwoven fabrics.

These impregnated nonwoven fabrics can be made in a variety of ways. For example, dry particles can be hydroentangled between two previously formed nonwoven fabrics. Alternatively, dry particles can be introduced while the fibers are being formed during meltblowing or spunbonding. It is also possible to entangle resin particles while wet using wet laying processes. In one embodiment, the particles are impregnated into an already formed fibers by hydroentanglement and there would be no melt bonding of the particles with the polymer fiber matrix.

One preferred fabrication method is the direct calendering of already prepared nonwoven fabrics that could be either meltblown or spunbonded. In one embodiment, the nonwoven fabrics is spread uniformly with particles that are delivered at a fixed mass rate by direct calendaring so that the membrane is covered with a given mass of particles per unit area. Once the particles are spread, a second membrane is placed over the first to make a sandwich and the combination is passed through a calendering roll with a pattern that is able to bond the two membranes together at low temperature and pressure. Particle densities on the surface are in the range of about 0.1 to about 10 gm/m2 or more. The pore size of the membranes used for this device allows larger entities such as, for example, red blood cells to pass through since their pore size is larger than 10 µm. The particles in the membrane are attached to a ligand that facilitates binding of the particles to target agents such as, for example, prion proteins from red blood cell concentrate and plasma.

The operation of the calendering process usually requires a high temperature for the bonding of the nonwovens, but the temperature is kept below the melting temperature of the particles and does not affect their performance. In one embodiment, larger or denser particles might be placed between the nonwoven membranes by hydroentanglement.

The density and weight of the nonwoven fabric can take on a wide range of values to ensure a high particle density on the fabric while maintaining the desired pore dimensions. Particle concentrations of approximately 60% w/w can be impregnated into the fabrics. All common methods of making nonwoven fabrics can be used for this procedure, including fabrics with two different polymer fibers as well as co-extruded fibers with two different polymers. Because of this flexibility, both wet and dry resins can be impregnated. If necessary, chopped fibers can be embedded into the fabric to facilitate the capture of the particles while still allowing flow pores of the necessary dimensions.

Chopped fibers are usually less than ½ inch long, and they are prepared by cutting a single fiber that is wound around a spindle or roll. The chopping is achieved mechanically using rotating blades or other sharp cutting surfaces. Chopped fibers can be made from a variety of polymeric or carbon fiber having a range of diameters from very small (less than about 1 µm) to large (>100 µm). In one embodiment, specific ligands are chemically grafted or coated on the fiber and then the fiber is cut to lengths of approximately ½ inch. Chopped fibers can then be distributed over a single layer of nonwoven fabric (polypropylene or other polymer) with a pore size and fiber diameter suitable to allow large entities such as red blood cells, to pass through the membrane (>10 µm pore sizes).

Chopped fibers can be delivered to the membrane at a prescribed rate to ensure uniformity in the distribution of fibers. Once chopped fibers are on the surface, a second layer of nonwoven fabric can be placed on top of the chopped fibers and the combination can be passed through a calender to bond the two nonwoven layers. In one embodiment, a porous matrix membrane or chopped fibers are functionalized with a ligand and is placed within another membrane, by for example air lay technology. In another embodiment, the ligands are attached to a polymer that is subsequently extruded into a fiber. The fiber can be chopped to make small segments that could be readily integrated between two membranes.

5. Surface Modification

Also included within the scope of the present invention are surface modified nonwoven or woven fabrics (SMNs) and surface modified particles that are functionalized on one or more internal and/or external surfaces with a reactive group. Functionalization is achieved by addition of one or more reactive groups to a surface of the porous matrix (e.g., woven or nonwoven fabrics), particles or both. The reactive group interacts with and binds the target agent. The interaction between the reactive group and the target agent is a chemical, physical and/or a biological interaction.

In one embodiment, the porous matrix, the particles or both are surface modified with a functional group capable of forming a covalent chemical bond with a target agent. Functional groups useful within the scope of the invention include, but are not limited to, one or more of the following groups, epoxy, formyl, tresyl, hydroxysuccinimide esters, among others. Other groups useful within the scope of the invention include, but are not limited to, one or more of the following groups, sulfonic acid, quaternary amines, carboxylic groups, primary amines, cyano, cyclohexyl, octyl, and octadecyl groups, oxirane, N-hydroxysuccinimide esters, sulfonyl esters, imidazolyl carbamate, quaternary amines, carboxylic groups, dye ligand, affinity ligand, antigen-antibody, nucleic acid molecules, groups for ion exchange, chelation, oxidation/reduction reactions, steric exclusion reactions, catalysis reactions, hydrophobic reactions, reverse phase, and other reactions normally encountered in chromatographic separations.

The functional group, for example ligands, are chemically conjugated to the support or can be attached via linkers, such as streptavidin, beta alanine, glycine, polymers containing glycine-serine, short chain hydrocarbons of the formula—$(CH_2)$—, polyethylene glycol, epsilon amino caproic acid, and linkers comprising—$O(CH_2)n$, wherein n is 1-30. If desired, the ligand(s) can be attached by one or by several different cleavable linkers, e.g., photolabile or acid labile moieties, enabling the selective detachment of a population of ligands for analysis. Detached ligands can be used, for example, as affinity purification media for proteins and enantiomeric separation (e.g., to concentrate, isolate, detect, characterize, quantify, or identify targets in a sample), as diagnostic therapeutic tools, catalysts and enhancers of chemical reactions, and as selective stabilizers of proteins.

In one embodiment, nonwoven membranes are coated with affinity ligands as a functional group, which affinity ligands have specific affinity for prions on their surface. The example of affinity ligands includes, a primary amine with a hydrophilic spacer containing polyethylene glycol units. The ligands can be placed on the membrane (e.g., plasma treated polypropylene from Macopharma) through chemical grafting or by a latex emulsion coating method (padding).

5.1. Polymerization of Ligands on Porous Matrix

Polymerization of monomers on a porous matrix introduces epoxy groups on the surface of these matrices, which in turn facilitates chemical attachment of the ligand to the surface of the matrix. In one embodiment, a monomer emulsion is applied onto cotton, polypropylene, polyester, and nylon fabrics by padding. Padding is a continuous process that is used in the textile industry for dying, bleaching, and coating of fabric. Additional information on padding is found in the Celanese LLC web site: www.vectranfiber.com, incorporated herein by reference. Padding in general consists of a set of squeeze rollers used to impregnate a fabric with a liquid by continuous passage of fabric through the liquid and then between the rollers to squeeze out excess solution. It is possible to use a single-dip, single-nip padding technique. Habeish et al., IMPROVING COTTON DYEING AND OTHER PROPERTIES BY EMULSION POLYMERIZATION WITH GLYCIDYL METHACRYLATE, *American Dyestuff Reporter*, Apr., 26-34 (1986), incorporated herein by reference) have applied glycidyl methacrylate (GMA) emulsions to cotton fibers using padding techniques. After padding, the excess water is evaporated and the polymerization is carried out at elevated temperatures. The amount of polymer on the fiber surface is in the range of from about 1 to about 10% or more. The polymerization can also be carried out on nonwoven webs of PET, PP, etc. with the desired pore size (>10 μm).

5.2. Latex Coatings on Fabrics

Latex emulsions are synthesized by convention emulsion polymerization, in water to make small particles of the desired polymer. Various soluble and free radical initiators and non-anionic and anionic surfactants can be used to create the emulsions. In one embodiment, the latex emulsions is coated on the porous matrix by padding as described above on either single fibers or nonwoven webs of PP, PET, and other polymers. An example of this type of approach is provided by De Boos and Jedlinek, APPLICATION OF EPOXY FUNCTIONAL POLYACRYLATE EMULSION TO TEXTILES, *J. Macromol. Sci-Chem. A*17 (2), 311-235 (1982), incorporated herein by reference.

6. Methods of Use

The methods, kits and devices of the invention are useful in a variety of applications including prognostic, diagnostic, detection, purification, separation, processing of expressed in vitro gene products, and production and delivery of biopharmaceuticals. This invention is applicable to any device that is commonly available for membrane operations, from flat plate, spiral wound or even hollow fiber cartridge devices. Flow can be induced through the device by any common means, from gravity to pumps, depending on the pressure drop and flow rate desired.

The purification and extraction techniques of the invention offer advantages over conventional purification techniques, by reducing the number of purification steps, improving yields, increasing purity, and overcoming limitations associated with the traditional methods.

The devices of the invention are highly sensitive capable of separating minute amounts of pathogens from a sample. In one embodiment, the devices of the present invention are used for the removal of pathogens such as prions including $PrP^c$, $PrP^{sc}$, $PrP^{res}$, viruses, bacteria and toxins from whole blood, red blood cell concentrates, platelets concentrates, plasma, plasma derivatives, leukocytes, leukodepleted blood, mammalian cell culture, fermentation broths and other media used for the production and delivery of biopharmaceuticals and the preparation of therapeutics. Multiple pathogens can be separated from the sample concomitantly and rapidly by the devices of the present invention from any stream in the plasma processing industry aimed at the production of therapeutic and/or pharmaceutical products.

In particular, the methods and devices of the present invention optimize the protein purification process and improve the manufacturing process of biopharmaceuticals by increasing efficiency and purity. Biopharmaceuticals are drugs that are proteins, peptides or other complex polynucleotides or protein based macromolecules (collectively "gene products"). Their manufacturing process involves the recovery of the desired gene product from its host biomass, such as plasma or other human and non-human biological sources (e.g., recombinant or non-recombinant cell cultures, milk of transgenic animals or recombinant or non-recombinant plant extracts). Separating commercially viable yields of the desired protein from a biomass is challenging since the latter contains unwanted host proteins, nucleic acid molecules and other naturally occurring chemical entities.

Protein separation and purification processes present unique challenges due to the variety of proteins, the different nature of possible contaminants and impurities, and the quantity of product to separate from the media. Conventional purification technologies generally involve a series of purification steps. With each step, the yield decreases and manufacturing costs increase. Protein separation and purification costs typically represent over 50% of the total manufacturing costs.

In another embodiment, the devices of the invention are designed so that they perform two simultaneous operations: filtration as well as adsorption. In this embodiment, the fabric pore size is reduced sufficiently to reject large particulate material while at the same time maintaining a pore size large enough to allow passage of the sample containing the desired molecule. This technology achieves simultaneous filtration and adsorption steps in a single device and replaces membrane filtration followed by adsorptive column chromatography. For example, the devices of the invention make it possible to adsorb a desired or an undesired molecule secreted extracellularly directly from a culture medium.

In another embodiment, the devices of the invention are used as an alternative to columns for adsorptive removal techniques in the biotechnology industry. These techniques utilize biochemical interactions such as, for example, ion exchange, chelation, oxidation/reduction reactions, stearic exclusion, catalysis, hydrophobic interaction, reverse phase, dye ligand, affinity ligand, antigen-antibody and other interactions normally encountered in chromatographic and/or other separation techniques.

7. Test Kits

Also encompassed within the scope of the invention are test kits for sample purification by separation of target agents from the sample.

Complete test kits contain solutions and devices for target separation and purification of biological samples. For example, the test kit contains a 96, 384, or 1536 well plate for high throughput sample purification, and/or solutions for attachment of ligands to the particles within the device of the invention in order to customize individual proteins, antibodies, and solutions required for protein separations in a plate format.

Generally, the test kits of the invention contain one or more of the following: (1) one or more containers containing the devices as described herein; (2) instructions for practicing the methods described herein; (3) one or more assay component; and (4) packaging materials. The devices described herein are packaged to include many if not all of the necessary components for performing the separation methods of the invention. For example, test kits include the device containing the porous matrix and particles in addition to one or more of the, buffers, reagents, chemical agents, functionalization reagents, enzymes, detection agents, control materials, or the like, among others.

In one embodiment, the kit additionally contains the functional groups in separate containers, and the functional groups would have to be attached to the particles and/or porous matrix prior to performing an assay. Alternatively, the device may be provided in the kit without functional groups, in which case the porous matrix, particles, or both are preferably pre-functionalized.

The devices of the invention can be of any desired size and shape. Preferably the device is a sheet-like material which, for example, is in a disk or strip form. Other items which may be provided as part of the test kit include solid surface syringes, pipettes, cuvettes, and containers. Coating the porous matrix or particles with monolayer materials or thicker materials provided by in-situ cross linking of polymers or covalently bonding functional molecules on the surfaces of the porous matrix or particles allows the optimization of both chromatographic selectivity and separation efficiency.

Detection can be facilitated by coupling the porous matrix, particles, or both to a detectable agent. Examples of detectable agents include, but are not limited, to various enzymes, prosthetic groups, fluorescent materials, luminescent materials, bioluminescent materials, radioactive materials, disperse dyes, gold particles, or a combination thereof.

EXAMPLES

It will be understood by one of ordinary skill in the relevant arts that other suitable modifications and adaptations to the methods and applications described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Surface Modified Nonwoven Fabrics (SMNs)

Surface modified nonwoven fabrics are specifically useful when the target species to be adsorbed is large, and it is unable to penetrate the pores of the resins. In this instance, the surface of the fibers comprising the nonwoven fabric was modified to affect the adsorption of the target agents. The adsorption step involves ion exchange, hydrophobic, or affinity interactions or any other common adsorption processes. If SMN is used without the particles, the surface area per unit volume of material available for attachment is controlled by the porosity of the fabric and the diameter of the fibers, $$a_v = \frac{4}{d_f}(1-\varepsilon) \tag{2}$$

Wherein $\alpha_v$ is the specific surface area per unit volume of solid, $d_f$ is the fiber diameter, and $\varepsilon$ is the void fraction.

Since fiber diameters anywhere in the range of 100 nm to 10 µm are available, and porosities normally are in the range of 0.4-0.5, very large surface areas can be achieved in these devices. For example, with a fiber diameter of 0.1 µm, the surface area per unit volume of fabric would be on the order of, $$a_v = 2\times 10^7 \text{ m}^2/\text{m}^3 = 20 \text{ m}^2/\text{cm}^3 \tag{3}$$

This compares quite favorably with the surface area per unit volume of many porous chromatographic supports. However, since the mean pore flow diameter of the fabric can be controlled independently, the pore sizes can reach several microns in diameter. Techniques such as electrospinning are able to produce even smaller diameters, resulting in much larger areas per volume.

Any surface modification that facilitates binding of a target agent to the device and is compatible with the chemistry of the specific porous matrices used in the device is encompassed within the scope of the invention. Surface modification includes, for example, the formation of charged species, the attachment of affinity ligands, peptides, oligonucleotides, proteins, spacer arms, hydrophobic moieties, fluorinated materials, among others.

Since the surface of the fibers in nonwoven fabrics tend to be smooth, these surfaces present a preferred configuration for the exposure of affinity ligands to a particular large species such as prion proteins, a virus or a bacterium.

Example 2

Device Configuration for Prion Protein (PrP) Removal

This example demonstrates the possibility of designing different device configurations to remove endogenous transmissible spongiform encephalopathy infectivity by allowing adsorption to non-porous surfaces of various geometries. Endogenous infectivity from red blood cell concentrates involves the removal of infectious $PrP^{sc}$ (scrapie form of the prion protein) or $PrP^{res}$ (resistant form of the prion protein) at a total concentration of approximately 200 ng/ml. In a bag of red blood cell concentrate (rbcc) containing 350 ml, there was a total of $7\times 10^{-5}$ g of PrP. Given that a monolayer of protein coats a surface with a monolayer of density of approximately 2 mg/m², the total surface area required for binding all of the endogenous PrP in rbcc is estimated as follows.

$$A = \frac{7\times 10^{-5} g}{2\times 10^{-3} g/m^2} = 3.5 \times 10^{-2} m^2 \tag{4}$$

Wherein A is the total area of the device.

As it is evident from the equation above, the total surface are required for binding prions is relatively small and accommodates several device geometries suitable for exposing affinity ligands at the correct surface density.

A. Square Sheets

A set of N square sheets of nonwoven fabric having both sides coated with ligands exposed to the blood has a total surface area given by, $$2NL^2 = 3.5 \times 10^{-2} \, m^2 \quad (5)$$

Wherein N is the number of sheets, and L is the length/width of a square sheet. In the case of 10 sheets (N=10), the required width of each sheet would be, $$L = 0.042 \, m = 4.2 \, cm \quad (6)$$

Figure 2:
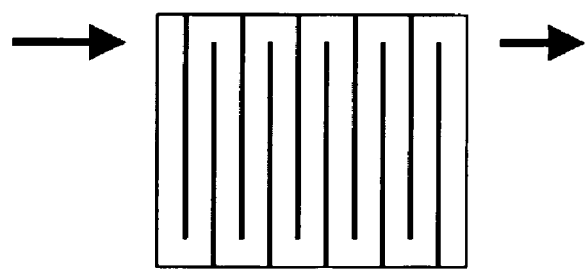

A device of this type consists of a staggered array of sheets with the fluid flowing in the tortuous path between sheets, as demonstrated in FIG. 2.

B. Coated Fibers

A set of N nonwoven fibers coated with affinity ligands on the outside have a total surface are given by, $$N2\pi RL = 3.5 \times 10^{-2} \, m^2$$

$$NRL = 5.57 \times 10^{-3} \, m^2 \quad (7)$$

Wherein R is the radius of a fiber.

For example, the number of fibers of radius of 5 µm and length 5 cm would be, $$N = 22,280 \quad (8)$$

The volume of these fibers would be, $$V_f = N\pi R^2 L = 8.74 \times 10^{-8} m^3 \times \frac{10^6 \, ml}{m^3} = 0.087 \, ml \quad (9)$$

Wherein $V_f$ is the volume of fibers.

As it is evident from the equation above, the volume of the fibers were relatively small, which is primarily due to the very small fiber diameter that gave rise to a very high surface area per unit volume. In order to allow proper flow of red blood cells through such a fiber mat, the porosity would have to be fairly high, for example about 50%. In this case, the volume of the device would be roughly twice the fiber volume or 0.17 ml. This is a very small volume, again indicating that a device for this type of capture does not need to be large to meet the capacity requirements. For example, a fiber mat of 2 cm radius would only have to be approximately 0.135 mm thick to provide this volume. One or more sheets of fibers can be coated with affinity ligands on the outside.

C. Particles

Small non-porous particles also exhibit a very high surface area per unit volume.

The number and volume of the particles required to have the surface area stated above was computed in a manner similar to that used in the case of cylindrical structures, $$N = \frac{3.5 \times 10^{-2} m^2}{4\pi R^2} \quad (10)$$

$$V_s = \frac{4}{3} \pi R^3 N$$

Wherein, Vs is the volume of a particle.

Given particles of radius 10 µm, the numbers and volume of particles given by equation 5 are, $$N = 2.79 \times 10^7$$

$$V_s = 1.17 \times 10^{-7} \, m^3 = 0.117 \, ml \quad (11)$$

The equation shows that an extremely small volume of small particles. Small particles could be dispersed with larger particles or suspended in a cross-linked gel (such as agarose) with large pores to allow easy flow of red blood cells through the system.

Example 3

Bonding Two Layers of Membranes by Calendering with or without Resin

In order to develop a prion removal device, two layers of polypropylene membranes were calendered successfully under room temperature/400 PLI and 150 F/100 PLI, with resin density at 1 mg/cm². Calendered membranes were sealed using an ultrasound sealer. The percentage of hemolysis from calendered membrane samples was well within the acceptable limit. Calendering was used for impregnation of Amino 650M resin between two membrane layers.

Toyopearl Amino 650M resin particles were impregnated between two layers of nonwoven fabric membranes. Polypropylene (Inner layer) and polyester (Outer layer) membranes that are currently used in MacoPharma leucofilters were good candidates for these membranes since they have already been approved for processing human blood.

In order to investigate whether particles could be immobilized without hindering the flow of red blood cells through the device, the inner and/or outer layer membranes were calendered with or without particles. Calendering was achieved by pressing membranes between two rollers into sheets.

Materials And Methods

One roll of polypropylene membrane (PP) and one roll of polyester membrane (PET) were wound on a 3-inch internal diameter plastic spindle. The width of the rolls was about 0.5 meters. The membranes were 22.5 cm wide and 800 m long. Membranes were cut into 22.5 cm×22.5 cm square sheets. Dry resin was spread at 1 mg/cm² on one side of membrane, and then covered with another membrane. Membrane alone samples did not need the resin spread. The above samples were passed through two calender rolls, one embossed roll and one smooth roll. Both rolls can be heated to increase temperature for calendering. The pressure between the rolls was also controlled. Calendered samples were tested by visual examination, weight measurement, cross-section examination by SEM (scanning electron microscopy) pore size test, and percent hemolysis test of flow through after passing whole blood through calendered device.

Procedure for Measurement of Percent Hemolysis

Membrane samples were cut into 25 mm circles, and placed into Millipore Swinnex 25 mm filter holders. Each sample was tested in duplicate on flow through, and then triplicate on 96-well plates. Each sample was rinsed with 2 ml working buffer (working buffer is 20 mM citrate and 140 mM NaCl, pH 7.0), then whole blood was pumped through membranes from the top at 0.5 mL/min. Five ml of flow through were collected from each sample. Flow through or untreated blood was centrifuged at 12000 rpm for 10 min at 4° C. to take the supernatant. Three 100 µL aliquots from each sample were placed into three wells of a 96-well plate. The UV absorbance of each plate was read at 415 nm. The average value of $A_{415nm}$ was divided by the value from 100% lysis of the same blood. The percentage of hemolysis is acceptable if it's below 1%.

Results

TABLE 1

Conditions used for calendering and visual examination

| Sample No. | Membranes calendered | Resin | Temperature (F.) Embossed roll | Smooth roll | Pressure (PLI)* | Results |
|---|---|---|---|---|---|---|
| 1 | Inner/Inner layer | Yes | cold | cold | 100 | with big area of pocket |
| 2 | Inner/Inner layer | Yes | cold | cold | 200 | with medium area of pocket |
| 3 | Inner/Inner layer | Yes | cold | cold | 300 | with small area of pocket |
| 4 | Inner/Inner layer | Yes | cold | cold | 400 | with isolated small area of pocket |
| 5 | Inner/Outer layer | Yes | cold | cold | 300 | barely bonded, big pockets |
| 6 | Inner/Inner layer | Yes | 120 | 120 | 100 | with small area of pocket |
| 7 | Inner/Inner layer | Yes | 140 | 140 | 100 | with isolated small area of pocket |
| 8 | Inner/Outer layer | Yes | 150 | 150 | 100 | not bonded well, big pockets |
| 9 | Inner/Outer layer | Yes | 150 | 150 | 200 | poorly bonded, some pockets |
| 10 | Inner/Outer layer | Yes | 180 | 180 | 200 | poorly bonded, some pockets |
| 11 | Inner/Outer layer | Yes | 180 | 180 | 400 | loosely bonded |
| 12 | Inner/Outer layer | Yes | cold | cold | 400 | barely bonded |
| 13 | Inner/Inner layer | Yes | 150 | 150 | 100 | very good, with little pocket |
| 14 | Inner/Inner layer | None | cold | cold | 100 | loosely boned, with pockets |
| 15 | Inner/Inner layer | None | cold | cold | 400 | tightly bonded without pockets |
| 16 | Inner/Inner layer | None | 157 | 153 | 100 | very well bonded |
| 17 | Inner/Inner layer | None | 157 | 153 | 400 | tightly bonded |
| 18 | Inner/Outer layer | None | 157 | 153 | 400 | loosely bonded |
| 19 | Outer/Outer layer | None | 180 | 180 | 400 | barely bonded, big pockets |
| 20 | Outer/Outer layer | None | 220 | 220 | 400 | bonded with some pockets |
| 21 | Outer/Outer layer | None | 220 | 220 | 600 | very well bonded |

*PLI = pounds per linear inch

From visual inspection, sample Nos. 4, 7, and 13 determined to be the best ones for particle embedment. When increasing the temperature of the rolls, a lower pressure can be used to bond the membranes as shown for samples 4 and 13. The outer layer membrane was made of polyester that was much thicker and stiffer than the inner layer. To calender the outer layer with either outer or inner layer membrane, higher roll temperatures and pressures were required as shown for sample 21.

TABLE 2

Weight measurement

Weight of calendered samples:

| Samples | Resin | Weight (gsm) |
|---|---|---|
| Single inner layer | | 41 |
| Single outer layer | | 67 |
| Inner/Inner layer calendered | | 82 |
| Inner/Inner layer calendered | 1 mg/cm2 | 92 |
| Inner/Outer layer calendered | | 107 |
| Inner/Outer layer calendered | 1 mg/cm2 | 117 |
| Outer/Outer layer calendered | 1 mg/cm2 | 129 |

For resin density, 1 mg/cm² equals to 10 g/m² (1 mg/cm²× $10^4$ cm²/m²=10 g/cm2). The weight from single layer, double layer and double layer embedded with resin was relatively proportional. The results showed that resin was well maintained between two layers of membranes.

The scanning electron micrograph (SEM) of samples 11 and 13 revealed that most resin particles were intact after calendaring, even though some were cracked. Sample 2 was also examined by SEM and revealed similar results. On the embossed roll of the calender, there were square grid spaces 2 mm×2 mm. During calendaring, the membranes were highly pressed where the grids touched. This area is referred to as the bonding area. The pocket area refers to an area that is farthest from the bonding area.

Figure 3:
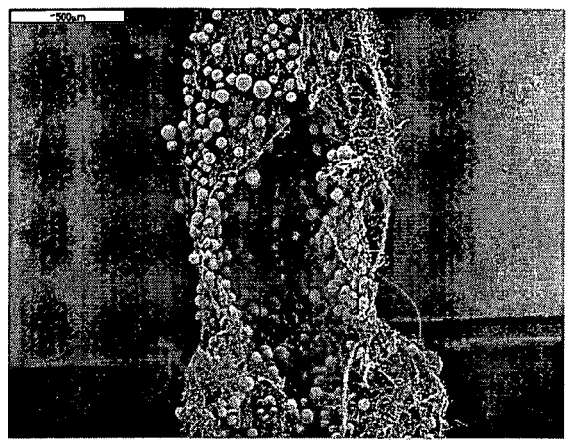
Figure 4:

Sample 11 is an example of immobilizing resin particles between one inner layer and one outer layer. FIG. 3 shows pocket areas of sample 11 at 50× magnification. Sample 13 is an example of immobilizing resin particles between two inner layers. FIG. 4 shows pocket areas of sample 13 at 50× magnification.

Pore Size Distribution

The results of the pore size distribution of calendered samples are shown in Table 3 below. For calendered samples, the smallest, mean, and largest pore sizes decreased 30% to 50% compared with the single layer. In order to determine whether the decrease in the pore size would hinder the passage of red blood cells through the device, further tests on the hemolysis of whole blood flow through were performed.

TABLE 3

Pore size distribution of calendered samples:

| Sample No. | Membrane | Resin | Rolls Temperature (° F.) Embossed | Smooth | Pressure (PLI) | Pore Size Distribution (μm) Smallest | Mean | Largest |
|---|---|---|---|---|---|---|---|---|
| 1 | Inner/Inner layer | Yes | Cold | Cold | 100 | 2.28 | 3.62 | 7.71 |
| 2 | Inner/Inner layer | Yes | Cold | Cold | 200 | 2.10 | 4.52 | 8.80 |
| 3 | Inner/Inner layer | Yes | Cold | Cold | 300 | 1.91 | 3.89 | 7.80 |

TABLE 3-continued

Pore size distribution of calendered samples:

| Sample No. | Membrane | Resin | Rolls Temperature (° F.) Embossed | Rolls Temperature (° F.) Smooth | Pressure (PLI) | Pore Size Distribution (μm) Smallest | Pore Size Distribution (μm) Mean | Pore Size Distribution (μm) Largest |
|---|---|---|---|---|---|---|---|---|
| 4 | Inner/Inner layer | Yes | Cold | Cold | 400 | 1.99 | 4.69 | 9.62 |
| 15 | Inner/Inner layer | No | Cold | Cold | 400 | 2.06 | 3.90 | 9.26 |
| 7 | Inner/Inner layer | Yes | 140 | 140 | 100 | 1.82 | 4.05 | 8.00 |
| 13 | Inner/Inner layer | Yes | 150 | 150 | 100 | 1.99 | 4.88 | 8.73 |
| 16 | Inner/Inner layer | No | 157 | 153 | 100 | 2.11 | 4.04 | 8.79 |
| PP | Single inner layer | | | | | 4.15 | 7.03 | 13.91 |
| 11 | Inner/Outer layer | Yes | 180 | 180 | 400 | 1.12 | 3.32 | 7.99 |
| 18 | Inner/Outer layer | No | 157 | 153 | 400 | 1.64 | 3.45 | 8.65 |
| 21 | Outer/Outer layer | No | 220 | 220 | 600 | N/A | 17.76 | 47.35 |
| PET | Single outer layer | | | | | 23.61 | 35.81 | 79.04 |

Example 4

Optimization of Calendering Using High Particle Densities

The calender roll used in this trial was ordered by ProMetic from BF Perkins. The roll is made of stainless steel, engraved with a honeycomb pattern, and coated with Teflon release coating. The back roll used was rubber coated (¾" to 1" thick).

Four-gram samples of dry resin were spread manually into 30 cm×20 cm (600 cm$^2$) swatches of plasma-treated polypropylene membrane, which corresponds to a particle density of 6.6 mg resin/cm$^2$. A second swatch of membrane was placed on top of the resin layer, and the sandwich was passed through the calender rolls at 10 m/min. The following table contains the results obtained during the tests.

TABLE 4

Calendering optimization results

| Trial | Set temperature (° F.) | Measured temperature (° F.) | Gap[1] (μm) | Results |
|---|---|---|---|---|
| 1 | 212 | 198 | 203 | No binding with or without particles |
| 2 | 230 | 215 | 0 | Membranes were weakly fused |
| 3 | 245 | 236 | 0 | Better than previous, but still too weak |
| 4 | 255 | 245 | 0 | Good binding without resin, but less efficient with resin |
| 5 | 260 | 248 | 0 | Good results with and without resin |
| 6 | 275 | — | 0 | Temperature was too high, top membrane did not fuse to bottom, but adhered to the roll |
| 7 | 265 | — | 0 | Good results were achieved at this temperature with and without resin |

[1] A zero gap indicates that the pattern penetrates the bottom roll by a 1/1000 of an inch.

The samples were observed under the microscope, and showed no pinholes. A swatch of each trial was kept (only without resin) for future reference.

Example 5

Binding of a β-Lactoglobulin and Flow Characteristics of Resin-Impregnated Calendered Membranes This experiment was conducted to determine the breakthrough curves for the binding of a model protein (β-lactoglobulin) to calendered membrane materials containing dry resin at a density of 4 mg/cm$^2$.

Polypropylene membrane material was calendered at 170° F. and 150 pounds per linear inch (PLI) containing dry resin at a density of 4 mg/cm$^2$. This membrane material was cut and assembled into Millipore Swinnex filter units. Each filter unit contained a stack of 1 to 4 membrane layers plus a layer of non-calendered membrane at the exit side of the filter unit. A solution of 0.5 mg/mL β-lactoglobulin in 1×PBS was passed through the filter unit at 1.5 mL/min using a peristaltic pump. Fractions of 0.5 mL were collected for 4 minutes and analyzed for their protein concentration using the Pierce Micro BCA assay kit (Pierce, Rockford, Ill.).

Figure 5:
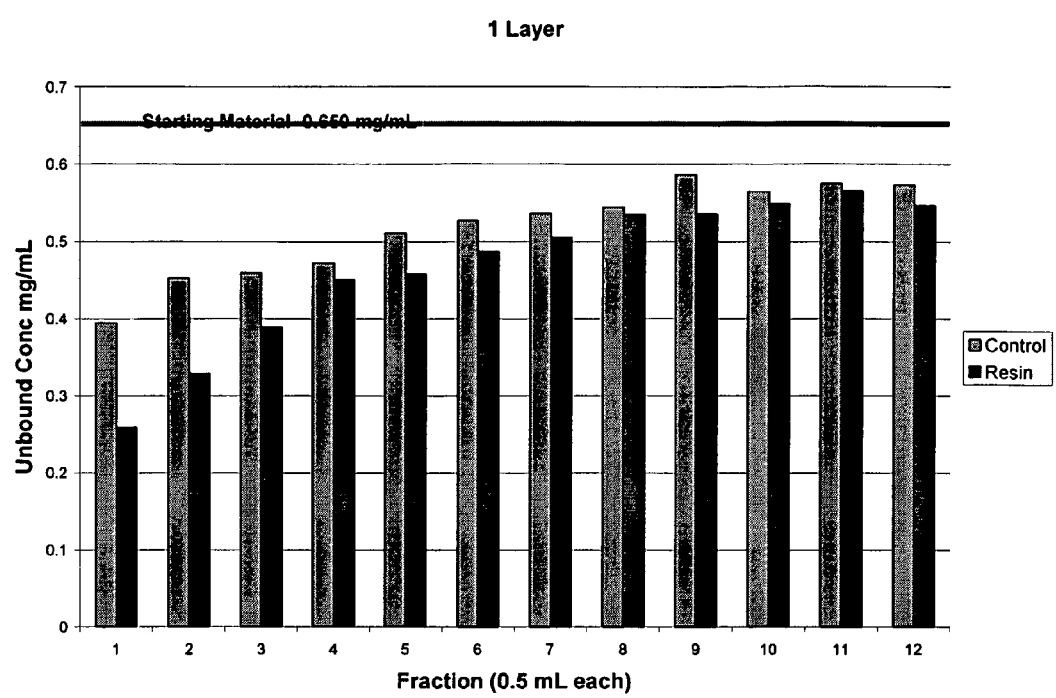
FIG. 5 Depicts a bargraph indicating the results of a Micro BCA assay of 12 fractions collected for the different number of membrane (porous matrix) layers. Different β-Lactoglobulin concentrations were showed on flow-through fractions of a solution passing through 1 layer of resin-embedded membrane (labeled "resin") or one layer of membrane (labeled "control").
Figure 6:
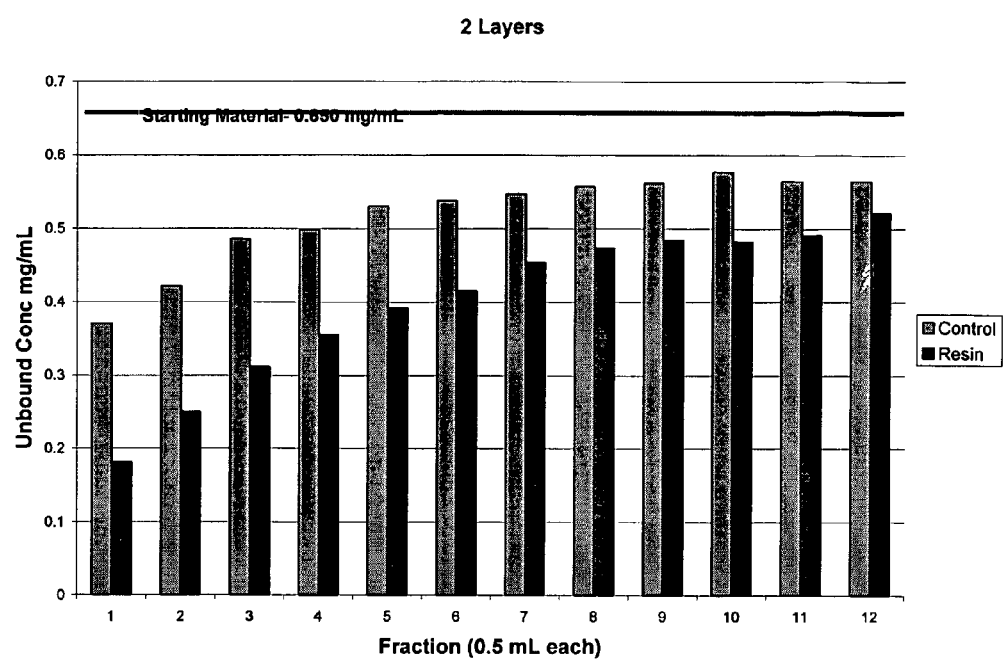
FIG. 6 Depicts a bargraph indicating the results of a Micro BCA assay of 12 fractions collected for the different number of membrane layers. Different β-Lactoglobulin concentrations were showed on flow-through fractions of a solution passing through 2 layers of resin-embedded membrane (labeled "resin") or 2 layers of membrane (labeled "control").
Figure 7:
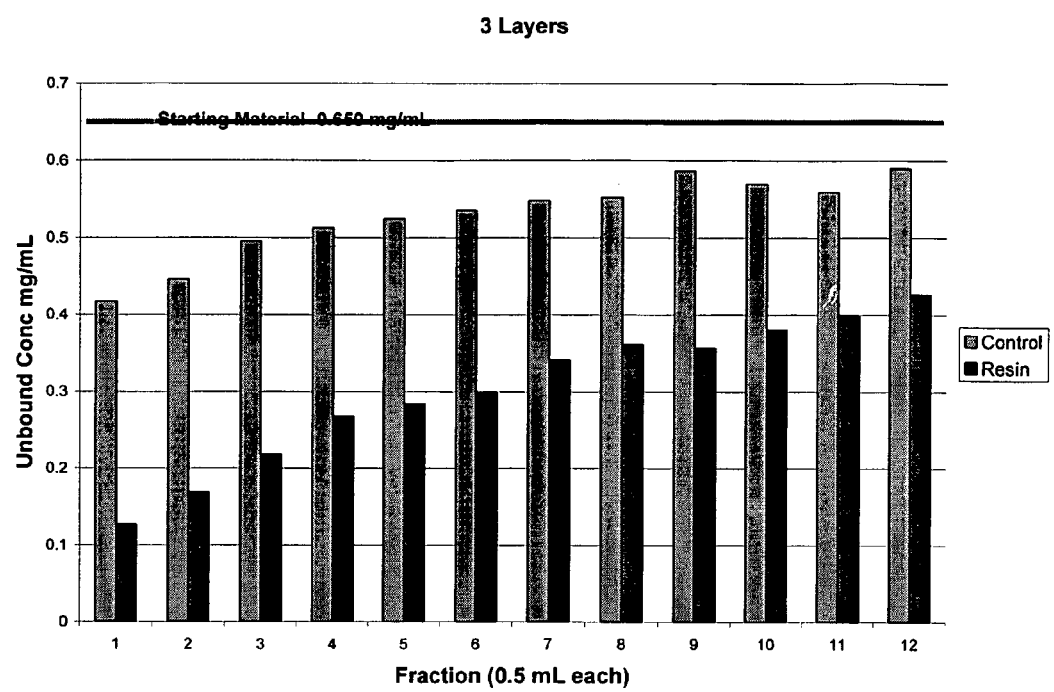
FIG. 7 Depicts a bargraph indicating the results of a Micro BCA assay of 12 fractions collected for the different number of membrane layers. Different β-Lactoglobulin concentrations were showed on flow-through fractions of a solution passing through 3 layers of resin-embedded membrane (labeled "resin") or 3 layers of membrane (labeled "control").
Figure 8:
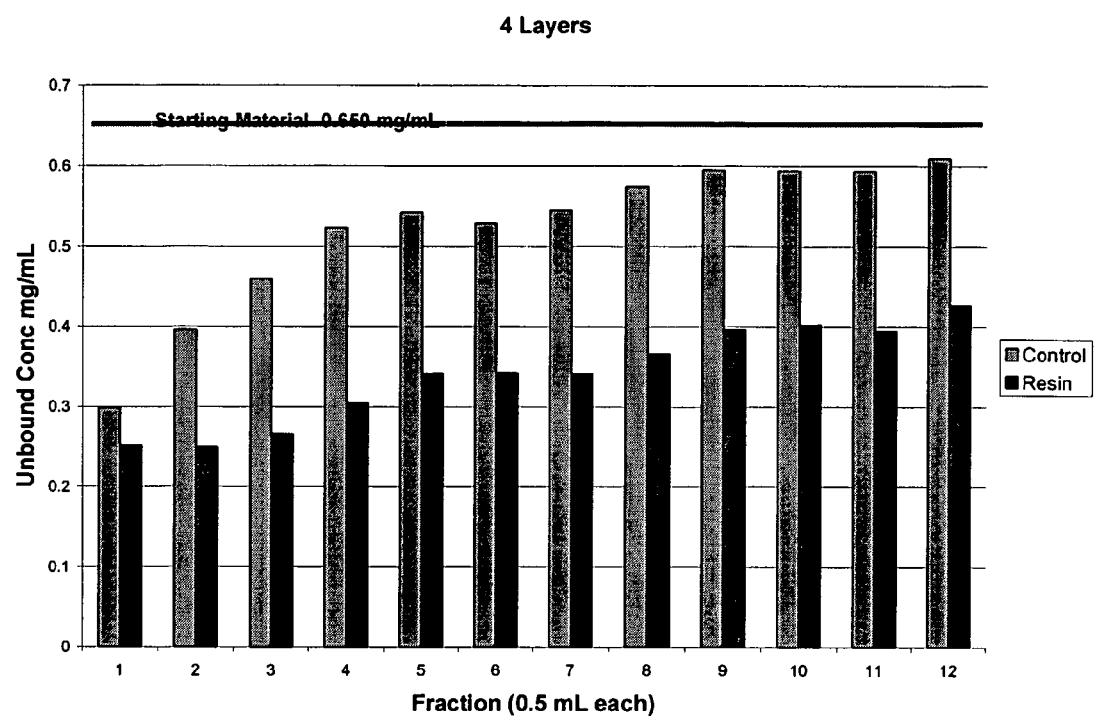
FIG. 8 Depicts a bargraph indicating the results of a Micro BCA assay of 12 fractions collected for the different number of membrane layers. Different β-Lactoglobulin concentrations were showed on flow-through fractions of a solution passing through 4 layers of resin-embedded membrane (labeled "resin") or 4 layers of membrane (labeled "control").

FIGS. 5-7 show the results of the Micro BCA assay of the 12 fractions collected for the different number of membrane layers. Calendered membrane without resin was used as the control. The results from this experiment show the difference in binding between the membrane with entrapped resin and the control. All of the runs displayed a similar initial slope of unbound concentration; however, layers 2-4 were not run long enough to show the saturated condition.

TABLE 5

Total bound protein and the amount of protein bound per weight of resin.

| Membrane | Total Protein Bound mg Control | Total Protein Bound mg Resin | mg bound/g resin |
|---|---|---|---|
| 1 Layer | 0.805 | 1.095 | 4.5 |
| 2 Layers | 0.792 | 1.493 | 5.4 |
| 3 Layers | 0.731 | 2.085 | 6.9 |
| 4 Layers | 0.776 | 1.859 | 4.2 |

The amount of protein bound in general increased for each additional layer of membrane peaking at three layers of membrane followed by a very small decrease with four layers (Table 5). Since the filters containing 2-4 layers of membrane were not run long enough to display saturated conditions it is not certain that they were done binding.

Example 6

Particle Distribution on Membrane Rolls

A particle spreading unit was developed to replace the manual distribution of beads used previously. The equipment has been tested and calibrated.

The powder applicator was manually set for 60%, which was equivalent to a dispensing rate of 6.52 to 6.99 Kg/hour (displayed). The measured dispensing rate determined by weight was 6.65 Kg/h (average of three determinations), within 5% of the target value of 6.96 Kg/hour.

Figure 9:
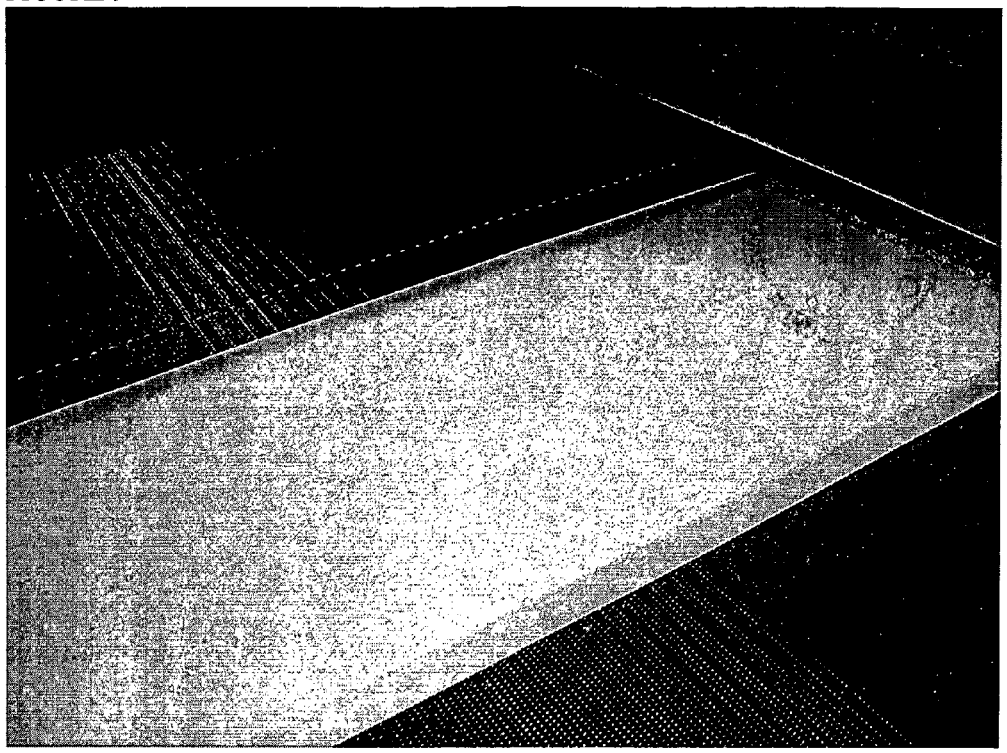
FIG. 9 Depicts distribution of particles on membrane rolls. Resin particles were dispersed uniformly onto the bottom membrane with no spilling over the edges of the membrane.

The powder dispensed appeared to be distributed with uniformity (visual evaluation) and no spilling over the edges of the membrane. FIG. 9 shows the distribution of particles onto the bottom membrane after running the line for about 1 hour. The sharp edges formed by the area containing the particles can be noticed on both sides of the membrane. Another noticeable feature is the lack of powder on the conveyor belt, even after some production time.

Example 7

Prions Binders

A list of resins used for binding prions is disclosed below.

a) Amino 650M—Base resin for coupling of peptide and other ligands. This base resin has demonstrated utility in binding of prion protein, both normal PrPc and infectious PrPsc (or PrPres). The resin was used in column chromatographic format and we have demonstrated removal/binding of PrPsc (hamster, mouse vCJD, mouse Fukuoka, human spCJD and Human vCJD) from red blood cell concentrate, plasma, whole blood to the limit of detection by in-vitro techniques (Western Blot) and a reduction in hamster 263K scrapie infectivity, i.e., in-vivo model (red blood cell concentrate) of approx. 4 logs.

b) Toyopearl-SYA—This tripeptide has demonstrated utility in binding of prion protein, both normal PrPc and infectious PrPsc (or PrPres). The resin was used in column chromatographic format and we have demonstrated removal/binding of PrPsc (hamster, mouse vCJD, mouse Fukuoka, human spCJD and Human vCJD) from red blood cell concentrate to the limit of detection by in-vitro techniques (Western Blot) and a reduction in hamster 263K scrapie infectivity, i.e., in-vivo model of approx. 4 logs.

c) Toyopearl-DVR—This tripeptide has demonstrated utility in binding of prion protein, both normal PrPc and infectious PrPsc (or PrPres). The resin was used in column chromatographic format and we have demonstrated removal/binding of PrPsc (hamster, mouse vCJD, mouse Fukuoka, human spCJD and Human vCJD) from red blood cell concentrate to the limit of detection by in-vitro techniques (Western Blot) and a reduction in hamster 263K scrapie infectivity, i.e., in-vivo model of approx. 4 logs.

The amino 650M, SYA and DVR have been used at full scale, i.e., 1 full unit of red blood cell concentrate passed over the resin (approx 350 ml). Column size was 10 ml of swollen resin. SYA, DVR, and amino function at 400 µmol/g (dry resin).

Example 8

Comparison of PrP$^{sc}$ Binding to Amino 650M and Amino 650U from SBH Spiked into Buffer, Filtered Plasma, and Whole Blood Amino 650U is a mixture of different bead sizes that includes Amino 650M and it is less expensive to produce than 650M. Amino 650U was tested for endogenous PrP and for its ability to bind PrP$^{sc}$ in all the matrices currently used, buffer, filtered plasma and whole blood and it was compared to binding with Amino 650M challenged with spiked whole blood. The experiment was designed to compare the binding of PrP$^{sc}$ from spiked buffer, plasma, and whole blood to Amino 650U and to establish binding of endogenous PrP$^c$ from plasma and whole blood to Amino 650U. Additionally, the experiment was designed to determine the effect of leukofiltration in the removal of PrP$^c$. Spiked buffer refers to the addition of brain homogenate to working buffer. Spiked whole blood is the addition of brain homogenate to human or hamster whole blood.

No difference in the signal was found for prion removal by 650 U or 650 M when present in plasma or whole blood. In conclusion amino 650 U and 650 M performed the same. The amount of PrP$^c$ removed by leukofiltration was more than that estimated to be in platelets and leukocytes together. Thus, it was possible that leukofiltration captured also some of the plasma-derived PrP$^c$. It has been shown that leukofilters behaved differently with regard to capture of human and hamster plasma-derived PrP$^c$. It is possible that while hamster plasma PrP$^c$ was not captured by the filter, human plasma PrP$^c$ was. Finally, it is also likely that the difference between the two results is due to lack of correlation between PrP$^c$ and infectivity.

The amount of PrP$^c$ removed by leukofiltration was more than that estimated to be in platelets and leukocytes together. Thus, it was possible that leukofiltration captured also some of the plasma-derived PrP$^c$. It has been shown that leukofilters behaved differently with regard to capture of human and hamster plasma-derived PrP$^c$. It is possible that while hamster plasma PrP$^c$ was not captured by the filter, human plasma PrP$^c$ was. Finally, it is also likely that the difference between the two results is due to lack of correlation between PrP$^c$ and infectivity.

Example 9

Binding of Hamster Brain PrP$^{sc}$ to AMN Resins

Comparative binding experiments were conducted for a series of resins (e.g., AMN-13, 14, 15, 16, and 17, Amino 650M and Amino 650U). AMN series relate to 650 U (newly designated as 650C-prdt) samples with varying amino substitution levels as follows:

| | |
|---|---|
| AMN-13; | 0.094 eq/L |
| AMN-14; | 0.078 eq/L |
| AMN-15; | 0.072 eq/L |
| AMN-16; | 0.063 eq/L |
| AMN-17; | 0.098 eq/L |

The resins bound to PrP$^{sc}$ from spiked buffer, plasma, and whole blood. The results demonstrated that all AMN resins bound equally well when challenged with both spiked buffer and spiked whole blood. Furthermore, the signal with AMN resins was the same as that with amino 650 M and 650 U. Comparing the resin binding of PrP from spiked plasma, there was a slightly more intense signal from Amino 650M compared to all other resins. Among the AMN resins #13 appeared to have weak PrP signal, but very comparable to amino 650 U while #15, 16, 17 all performed better than amino 650 U. No noticeable difference was observed between AMN 14, 15, 16, 17 resins.

In conclusion, the study demonstrated more similarity among the resins and most importantly it showed closer correlation with amino 650U than with 650 M. The differences observed with plasma suggested that at least with that challenge reducing the level of substitution may be beneficial and the resin performed more closely to amino 650 M.

Example 10

Extraction of Proteins Bound to Resin-Embedded Membranes and Determination of Binding of PrP$^c$ from Normal Hamster Brain Homogenate The development of the new device using resin-embedded calendered membranes lead to the need of developing new procedures for extraction of the bound proteins from the resins. Changes had to be made to the handling of the material, as well as the composition, concentration and volume of the extraction solution. The experiment was also designed to perform binding evaluations in the new format, using both Toyopearl Amino 650Mresin-embedded membranes and its fully acetylated form.

Normal hamster brain homogenate (HaBH) was treated with sarkosyl and spun down. The resulting supernatant was diluted to a final concentration of 1% using working buffer or human whole blood. Fifty milliliters of spiked solution was passed through 47 mm Swinnex filter holders (Millipore) containing 4 sandwiches of calendered membranes embedded with 4 mg/cm$^2$ of chromatographic resin at full capacity, or a reduced substitution capacity form of the same resin as a control either Toyopearl Amino 650M or its fully acetylated form. The flow rate used was 0.5 mL/min, using a peristaltic pump. Ten aliquots of 5 mL each were collected for each of the spiked solutions and membrane type. The flowthrough samples of both membranes challenged with spiked buffer were analyzed by ELISA. The membranes containing resinsfully acetylated resin and challenged with spiked whole blood were rinsed using working buffer.

Sections of membranes (in some cases the whole stack) were treated with either SDS-PAGE sample buffer or 99% formic acid. Treatment with formic acid consisted of adding 0.5 mL of 99% formic acid and 10 µL of 20% SDS to 1 quarter of a membrane sandwich, followed by incubation for 1 hour removal of the liquid, and evaporation using a SpeedVac. The samples had their volumes adjusted to 15 µL using water, followed by addition of 15 µL of 2× sample buffer. The treatment with sample buffer consisted of adding 3 mL of 1× sample buffer to the complete stack of membranes, followed by incubation for 30 minutes, and boiling for 7 minutes. The solution was harvested without pressing the membranes, and centrifuged briefly to remove all the resin. A variation of the above treatment was also tested. It consisted of adding 1 mL of 2× sample buffer to two separate stacks of membranes corresponding to ¼ of a filter, incubating for 1 hour, followed by boiling only one of them. Elution with sample buffer without boiling may be used if disassembling the filter holders becomes too risky when using infectivity.

A final condition tested was the incubation of sections (¼) of the membranes with sample buffer to verify binding to the first, second, third and fourth membrane to contact the challenge solution. Samples were then run on SDS-PAGE gels and stained for total protein. Western blots were also performed. The void volume of the filter holder was approximately 7 mL. After passing 50 mL of challenge solution through each of the filters, followed by air, the volumes recovered were 45 and 47 mL for whole blood. When using spiked buffer, the volumes recovered were 46 and 46 mL. There was no significant difference noticed when using the different challenge solutions.

The first filter holder to be open was the one containing the membrane with fully acetylated Toyopearl that was challenged with spiked whole blood. It was noticed that despite the passing of air and rinsing with buffer there was still some blood inside the filter. During the attempt to rinse the membranes with buffer, there was a significant loss of resin, and the membrane was discarded.

The filter holder with Toyopearl amino 650M challenged with whole blood was rinsed with an extra 200 mL of buffer. The flow rate was higher than max (999 in the dial). Upon opening the holder it was noticed that there was still some blood inside, especially between layers. It was also noticed that a couple sections delineated by the radial distributor were bypassed during the wash.

The stack of membranes was cut into 4 quarters. One of the pieces had the four layers separated and treated with sample buffer to investigate if the different layers had different binding. Another quarter was also separated into pieces and submitted to the formic acid treatment. The remaining two quarters were used to compare the treatments with and without heating.

The two filters challenged with spiked buffer were rinsed with 200 mL of working buffer each. The filters were opened and the whole stack was transferred to a small glass vial, to which 3 mL of sample buffer was added.

The resin embedded in the calendered membranes appeared to maintain the same PrP binding properties characteristic of the resin in column format. The fully acetylated amino showed weaker membrane-bound PrP signal compared to amino signal, supporting the conclusions that fully acetylated amino may not bind PrP efficiently. In general, the results indicated that 50% accetylation whether in a blend form or by chemical synthesis reduced the PrP$^{res}$ binding.

Example 11

Binding of PrP$^C$ from Normal Hamster Brain Homogenate to Filters Containing Particle-Impregnated Membranes The following experiment demonstrates the binding of normal PrP (PrP$^c$) from normal hamster brain homogenate (NBH) by membranes containing resin particles.

The elution method described in the previous example was applied to these samples. The filter was opened, the membranes were placed in a glass vial and incubated with mixing with 2 ml of NuPage sample buffer (Invitrogen corporation, Carlsbad, Calif.) The vial was then heated and the resin that came out of the filter was collected. Western blot results of the eluted proteins indicated that the method eluted PrP from the membrane. The results also indicates that the filters with the resins bound more PrP than the filter without the resin.

Example 12

Binding of PrP$^c$ from Scrapie Brain Homogenate to Filters Containing Particle-Impregnated Membranes This experiment demonstrates the performance of filters in binding PrP$^{sc}$ from infectious hamster brain homogenate (SBH) spiked into whole blood and in buffer. The filters contained membranes impregnated with full capacity resins, as well as reduced capacity resin, and no resin as control.

Elution was done with injecting 2 ml of NuPage sample buffer (according to extraction described in Example 10). Western blot of the eluted proteins showed strong signal without PK (protein kinase) but weak signals with PK. Since the proteins were eluted with 2% SDS, the PK digestion was conducted under 2% detergent concentration instead of 0.2% SDS (standard procedure). It is likely that the PrP$^{res}$ weak signal with PK is due to excess SDS in the reaction mixture. The results indicate weaker signal with the membranes without resin, but similar signal intensities for all other resins tested. No difference was observed between SBH in buffer and in whole blood for full capacity resins and no resins. Reduced capacity resin showed stronger signal with buffer spiked compared to blood spiked.

Example 13

Testing of Prototype Filter

In this example, the filters were assembled in plastic casings and welded together, in a configuration similar to a final device. The performance of such device was evaluated using various challenges, spiked and non-spiked. In one embodiment, the final device was composed of a rigid or pliable plastic casing containing layers of non-calendered membrane (from 1 to about 25 or more), followed by several layers (between 1 and about 50, depending on the desired capacity of the device) of resin-embedded membranes, and between 1 to about 25 layers of non-calendered membranes. The filters were welded together using an ultrasound cutter/sealer or by the use of a press to apply heat and pressure simultaneously. In this example, heat and pressure were used.

Hamster brain homogenate was treated with 0.5% Sarkosyl and diluted 100-fold in buffer, filtered plasma, and whole blood and used as the challenge to the resins. The resins were challenged with 80 ml of sample at 0.5 ml/min with a peristaltic pump. Western blots of the resin bound $PrP^{res}$ samples were conducted without PK digestion. The results indicated that the membranes performed well with the spike in buffer and in plasma but the same spike in blood appeared to be reduced.

Example 14

Removal of PrP from Spiked RBCC by a Series of Filter Devices

This experiment shows the removal of PrP from spiked red blood cell concentrate (RBCC) using a device containing particle-impregnated device. Since the device was challenged with an excess of target protein, a series of devices was used. The total volume of RBCC used was equivalent to one unit.

All filtrations went without any obvious problem and a pump was used for all filtrations. All filters had soft casings and were pre-tested for leakage. None of the filters leaked in the pre-test or in the actual experiment. The filtration time was about 10 minutes each for one unit of RBCC (~300 ml). Filters were washed with about 460 ml of working buffer (citrate). The efficiency of the washing step was empirically assessed by examining the color of the filter after washing.

After washing, the filters were injected with air to remove all liquid in the filter. The filters were treated with ~4.6 ml of sample buffer for elution (injected on one side of the filter). The sample buffer was collected and injected on the other side of the filter. This step was conducted three times. The results indicated that that $PrP^{res}$ escaped filter 1 and was captured by filter 2, which was expected, since the challenge applied was higher than the capacity of one filter set. $PrP^{res}$ could be also present in the eluate of filter 3 but be below the limit of detection of the Western blot. These results compared to those with RBCC in the first PRDT infectivity study indicate that the filters performed as well as the same resins used in a column format. As with the previous study, large excess of $PrP^{res}$ was passed through the filters and it is not surprising that not all $PrP^{res}$ was captured in the first filter.

Example 15

Grafting Glycidylmethacrylate on Polypropylene, Polyethylene Terephthalate, Cotton and Nylon Substrates Grafting is an efficient method to change surface properties of polymers. The grafted polymers tailored with specific ligands in combination with superior mechanical properties of the substrates make grafting the most versatile method for protein binding, whose applications often require change of ligands as well as enough mechanical strength. In this example, grafting of glycidylmethacrylate (GMA) on polypropylene (PP), polyethylene terephthalate (PET), cotton and nylon substrates were performed to show the possibility of applying this approach for $PrP^c$ removal from human blood.

Procedure:

The substrates used for the tests include cotton woven fabric, nylon woven fabric, PP non-woven fabric, PP non-woven membrane (Macopharma PP175), PP fibers and PET fibers from the College of Textile at NCSU.

Grafting was carried out by the following steps:

1. Samples were washed with acetone three times;
2. Samples were dried in a vacuum oven for more than three hours;
3. Samples were treated with Argon plasma for 15 s at 750 W;
4. Samples were exposed to air for 30 minutes;
5. Samples were then immersed in 10% GMA solution in a UV chamber for 6 hrs. The UV intensity was 1.1 $W/m^2$. The temperature of chamber was 30° C. and that of sample rack was above 60° C.;
6. After the UV polymerization, samples were then washed with acetone for three times;
7. Samples were dried in a vacuum oven.

At this stage, samples were only analyzed for their weight gain and IR spectrum. After analysis, the grafted PP non-woven fabric and PP non-woven membrane were further aminated in ammonia hydroxide solution at 60° C. overnight. These samples were then washed and dried for elemental analysis.

Results:

From the results of gravimetric measurement and IR spectroscopy, the PP substrates show significantly better grafting results than the other substrates, cotton, nylon and PET. Three types of PP substrates have been tested, PP fiber, PP non-woven and PP non-woven membrane (Macopharma). The weight gains after grafting are 85% 154%, and 57%, respectively (Table 6). These values are much higher than those (−3% to 4%) of the other substrates. These results are further confirmed by the IR spectra, where the grafted PP systems show strong peaks at 1720 $cm^{-1}$ related to the carbonyl group and at 845 and 910 $cm^{-1}$ related to the epoxide group, the signature for GMA. Other substrates did not show much change when comparing the blank sample with the samples after grafting.

The reasons for the differences of grafting on the various substrates are still not clear. One possible reason is that C—H bond might be easier to break in the PP environment than in the other environment. Another possible reason is that the nylon and cotton fabric samples might have had surface treatments unknown to us. Simply washing by acetone may not be sufficient to remove the finishing.

It is also interesting to note that for the original PP fiber and non-woven membrane (Macopharma PP175) samples show peaks in the 840 to 920 cm$^{-1}$ range. However, no such peaks are shown for the PP non-woven fabrics. The peaks for the former could be the results of oxidation of the sample surfaces, which are from processing at high temperatures.

From the IR spectrum, the aminated Macopharma sample shows broader peak at 3400 cm$^{-1}$ which is attribute to —OH and —NH$_2$ groups, the results of amination.

Determination of Surface Area of Non-Woven Materials

Determining surface area of non-woven materials is not easy task due to complex interlocks of fibers that forming the non-woven. However, surface area of a single fiber can be determined accurately by measuring microscopic images of the fiber and the length. Therefore, it is theoretically possible to measure surface area of non-woven materials through fibers of the same materials by grafting method, providing the surface properties of the fibers are same to that of the non-woven materials. This method can be expressed by the following equation:

$$Wt = D(S_f + S_{NW})$$

where Wt is weight gain from grafting, $S_f$ is surface area of fiber and $S_{NW}$ is surface area of non-woven material. Only two unknowns are in the equation: D and $S_{NW}$, which can be determined by two independent experiments.

The area determined by this method is the effective surface area corresponding to each type reaction. Actually, any reactions whose extents depend on the surface area of substrates can be used to for this method.

Conclusions:

Primary tests of grafting GMA on several polymer substrates show that PP is an ideal substrate for such grafting. The weight gain of grafting GMA on PP varies from 60% to 160%, depending on the shape of PP materials. The grafting effects are also confirmed by the FTIR spectra. Furthermore, based on grafting, a simply method has been proposed for measuring surface area of non-woven materials (Table 6).

TABLE 6

Effects of grafting measured in weight gain

| Sample Name | Substrate | UV Time (hr) | Initial Weight (g) | Weight Gain (%) |
|---|---|---|---|---|
| Co-g-GMA-032905 | Cotton woven fabric | 0.6 | 0.1283 | −1.8 |
| Ny-g-GMA-032905 | Nylon woven fabric | 0.6 | 0.1323 | −0.7 |
| PP-g-GMA-032905 | PP non-woven | 0.6 | 0.1179 | 1.7 |
| Co-g-GMA-033105 | Cotton woven fabric | 6 | 0.0954 | −2.8 |
| Ny-g-GMA-033105 | Nylon woven fabric | 6 | 0.1446 | −1.4 |
| PP-g-GMA-033105 | PP non-woven | 6 | 0.0537 | 91 |
| Mac-PP-g-GMA-040805 | Macopharma PP non-woven membrane | 6 | 0.0668 | 57 |
| NW-PP-g-GMA-040805 | PP non-woven Fabric | 6 | 0.0738 | 154 |
| FB-PP-g-GMA-040805 | PP fibers | 6 | 0.0789 | 85 |
| FB-PET-g-GMA-040805 | PET fibers | 6 | 0.0517 | 4 |

Example 16

Binding of PrP$^c$ by PGMA Fibers, Electro-Spun Web, PGMA Grafted and Padded PP Substrates Purpose:

To determine the binding of PrP$^C$ by PGMA fibers, electrospun web and GMA grafted and padded polypropylene non-wovens.

Procedure:

The materials tested were polyglycidylmethacrylate (PGMA) melt spun fibers, PGMA electro-spun webs, PGMA grafted and padded polypropylene (GMA-g-PP) nonwoven fabric. The substrates are samples from the College of Textiles at North Carolina State University, MacoPharma PP175, and Macopharma PP 235. For each material, two replicas were prepared for protein binding.

The samples were prepared in both weight and apparent area (the measured area of fabrics). The second method only applied to the samples with regular shapes, such as the padded MacoPharma membranes.

All the samples were chopped into small pieces. Each sample was then immersed into a conical tube (50 ml) containing 5 ml 1% normal hamster brain homogenate (HaBH) solution. Samples were then incubated on a rocking platform for 30 minutes. After that, the samples were washed with 10 ml sample buffer for three times of 10 minutes on the rocking platform.

Results:

Sample weight, area and animation level which was determined by elemental analysis are shown in the following in Table 7 below

TABLE 7

Elemental Analysis of Samples.:

| Name | | N % |
|---|---|---|
| | Weight (g) | |
| PGMA-Fiber A | 0.1009 | 3.8% |
| PGMA-Fiber B | 0.1011 | 3.8% |
| PGMA-g-PP A | 0.1007 | 2.6% |
| PGMA-g-PP B | 0.1009 | 2.6% |
| PGMA-g-PP (Maco175) A | 0.1011 | 1.5% |
| PGMA-g-PP (Maco175) B | 0.1010 | 1.5% |
| PGMA-p-PP1A | 0.1015 | Not available |
| PGMA-p-PP1B | 0.1007 | Not available |
| PGMA-p-PP2A | 0.1007 | Not available |
| PGMA-p-PP2B | 0.1012 | Not available |
| PGMA-p-PP3A | 0.1012 | Not available |
| PGMA-p-PP3B | 0.1007 | Not available |
| Blank-Nonwoven-PP A | 0.1009 | None |
| Blank-Nonwoven-PP B | 0.1011 | None |
| Blank-Maco175A | 0.1011 | None |
| Blank-Maco175B | 0.1006 | None |
| 650MA | 0.1016 | 0.6% |
| 650MB | 0.1011 | 0.6% |
| Electro Spun A | 0.1001 | Not available |
| Electro Spun B | 0.1005 | Not available |
| | Area ($cm^2$) | |
| PGMA-p-PP (Maco235) 6A | 4 × 4 | Not available |
| PGMA-p-PP (Maco235) 6B | 4 × 4 | Not available |
| PGMA-p-PP (Maco235) 7A | 4 × 4 | Not available |
| PGMA-p-PP (Maco235) 7B | 4 × 4 | Not available |
| PGMA-p-PP (Maco235) 9A | 4 × 4 | Not available |
| PGMA-p-PP (Maco235) 9b | 4 × 4 | Not available |
| PGMA-p-PP (Maco235) 10[a] | 4 × 4 | Not available |

TABLE 7-continued Elemental Analysis of Samples.:

| Name | | N % |
|---|---|---|
| PGMA-p-PP (Maco235) 10B | 4 × 4 | Not available |
| Blank-Maco235A | 4 × 4 | Not available |
| Blank-Maco235B | 4 × 4 | Not available |

Based on the results from western blot both PGMA grafted PP and PGMA padded PP bind prion.

EQUIVALENTS

The invention illustratively described herein suitably may be practiced in the absence of any element or elements, limitation or limitations which is not specifically disclosed herein. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed may be resorted to by those skilled in the art, and that such modifications and variations are considered to be within the scope of this invention as defined by the appended claims.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

What is claimed is:

1. A method of manufacturing a device for filtering and separating at least one target agent from a sample, said device comprising one or more stacked layers of resin-embedded membranes comprising first and second layers of porous nonwoven fabric that are bonded together with a plurality of resin particles impregnated therein or sandwiched therebetween, said porous nonwoven fabric having pore sizes greater than 10 µm, and the resin particles having a size of 40-200 µm, wherein the at least one target agent attaches to the porous nonwoven fabric, the resin particles or both, and is removed from the sample, which method comprises the steps of:
   (a) spreading the plurality of resin particles on a first layer of said porous nonwoven fabric,
   (b) placing a second layer of said porous nonwoven fabric over the first layer to form a double layer, and
   (c) calendering the double layer to form a resin-embedded membrane.

2. The method of claim 1, wherein the device further comprises one or more single layers of porous nonwoven fabric, said method further comprising arranging the one or more single layers of porous nonwoven fabric and the resin-embedded membranes in a stack.

3. The method of claim 2, wherein the device comprises about 1 to about 25 single layers of porous nonwoven fabric followed by between 1 and about 50 layer of resin-embedded membranes, followed by between 1 and about 25 single layers of porous nonwoven fabric, said method further comprising arranging the single layers of porous nonwoven fabric and the resin-embedded membranes in a stack.

4. The method of claim 1, wherein two or more layers of resin-embedded membranes are present, said method further comprising welding together the two or more layers of resin-embedded membranes.

5. The method of claim 4, wherein said welding is carried out using an ultrasound cutter/sealer or a press that applies heat and pressure simultaneously.

6. The method of claim 1, further comprising assembling the stacked layers of resin-embedded membranes in a plastic casing.

7. The method of claim 1, wherein the resin particles comprise a polymethacrylate or a methacrylate resin, a modified resin, or both.

8. The method of claim 1, wherein the resin particles comprise TOYOPEARL™ AMINO 650.

9. The method of claim 1, wherein the resin particles comprise a wet resin, a dry resin, or a combination thereof.

10. The method of claim 1, wherein the porous nonwoven fabric comprises polypropylene and/or polyester.

11. The method of claim 1, wherein the resin particles comprise a modified resin, the porous nonwoven fabric comprises plasma treated polypropylene and the reactive group comprises a ligand having a primary amine and a hydrophilic spacer containing polyethylene glycol units.

12. The method of claim 1, wherein one or both of the porous nonwoven fabric and the resin particles used to form the resin-embedded membrane during steps a)-c) is capable of attaching a prion protein.

13. The method of claim 12, wherein the prion protein is a normal form of prion protein or an infectious form of prion protein.

14. A method of manufacturing a resin-embedded membrane comprising first and second layers of porous nonwoven fabric that are bonded together with a plurality of resin particles impregnated therein or sandwiched therebetween, the method comprising the steps of:
   (a) spreading the plurality of resin particles on a first layer of said porous nonwoven fabric,
   (b) placing a second layer of porous nonwoven fabric over the first layer to form a double layer, and
   (c) calendering the double layer to form the resin-embedded membrane,
   wherein the porous nonwoven fabric has a pore size greater than 10 µm, the resin particles have a size of 40-200 µm, and the porous nonwoven fabric, the resin particles or both, are capable of binding to prion protein.

15. A method of manufacturing a device that includes one or more resin-embedded membranes, the method comprising:
   providing one or more resin-embedded membranes prepared according to the process of claim 14; and
   arranging the provided one or more resin-embedded membranes in a passage of the device.

16. The method of claim 15, wherein two or more resin-embedded membranes are provided and arranged in a stack in the device.

17. The method of claim 16, further comprising:
   providing one or more single layers of porous nonwoven fabric and arranging the provided one or more single layers of porous nonwoven fabric in the stack.

18. The method of claim 17, wherein said arranging is carried out using about 1 to about 25 single layers of porous nonwoven fabric followed by between 2 and about 50 layer of resin-embedded membranes, followed by between 1 and about 25 layers of porous nonwoven fabric, thereby forming the stack.

* * * * *